United States Patent
Beroz et al.

(10) Patent No.: US 6,361,959 B1
(45) Date of Patent: *Mar. 26, 2002

(54) MICROELECTRONIC UNIT FORMING METHODS AND MATERIALS

(75) Inventors: Masud Beroz, Livermore; Joseph Fjelstad, Sunnyvale; Belgacem Haba, Cupertino; Christopher M. Pickett, San Jose; John Smith, Palo Alto, all of CA (US)

(73) Assignee: Tessera, Inc., San Jose, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 09/317,675

(22) Filed: May 24, 1999

Related U.S. Application Data

(63) Continuation-in-part of application No. 09/267,058, filed on Mar. 12, 1999, application No. 09/317,675, which is a continuation-in-part of application No. 09/138,858, filed on Aug. 24, 1998, which is a division of application No. 08/440,665, filed on May 15, 1995, now Pat. No. 5,801,441, which is a division of application No. 08/271,768, filed on Jul. 7, 1994, now Pat. No. 5,518,964, application No. 09/317,675, which is a continuation-in-part of application No. 09/140,589, filed on Aug. 26, 1998.

(60) Provisional application No. 60/077,928, filed on Mar. 13, 1998, and provisional application No. 60/056,965, filed on Aug. 26, 1997.

(51) Int. Cl.[7] .............................. C12Q 1/54; C12Q 1/00
(52) U.S. Cl. ........................... 435/14; 435/4; 435/283.1
(58) Field of Search .................... 435/14, 4, 283.1

(56) References Cited

U.S. PATENT DOCUMENTS

| | | |
|---|---|---|
| 3,373,481 A | 3/1968 | Lins et al. ............ 29/471 |
| 3,374,537 A | 3/1968 | Doelp, Jr. ............ 435/14 |
| 3,460,105 A | 8/1969 | Birt et al. ............ 435/14 |
| 3,795,037 A | 3/1974 | Luttmer ............ 29/628 |
| 3,825,353 A | 7/1974 | Loro ............ 317/234 |

FOREIGN PATENT DOCUMENTS

| | | |
|---|---|---|
| EP | 0072673 A2 | 8/1982 |
| EP | 0 352 020 A3 | 1/1990 |
| EP | 0 433 997 A2 | 6/1991 |
| GB | 2151529 | 12/1983 |
| GB | 2142568 | 7/1984 |

(List continued on next page.)

OTHER PUBLICATIONS

"Method of Testing Chips and Joining Chips to Substrates," Research Disclosure, Feb. 1991, No. 322, Kenneth Mason Publication Ltd., England. IBM Technical Disclosure Bulletin, vol. 36, No. 07, Jul. 1993.
"Electronic Packaging and Interconnection Handbook," pp. 7.24–7.25; Harper. Research Disclosure No. 322 (Feb. 1991) "Method of Testing Chips and Joining Chips to Substrates," XP 000169195.
Adwill D–570M, D–628, D–675 data sheets, LINTEC Corporation.

*Primary Examiner*—Louise N. Leary
(74) *Attorney, Agent, or Firm*—Lerner, David, Littenberg, Krumholz & Mentlik, LLP

(57) ABSTRACT

Electrically conductive elements such as terminals and leads are held on a support structure by a degradable connecting layer such as a adhesive degradable by heat or radiant energy. After connecting these elements to a microelectronic element such as a chip or wafer, the conductive elements are released from the support structure by degrading the connecting layer. The support structure desirably has a predictable, isotropic coefficient of thermal expansion and such coefficient of thermal expansion may be close to that of silicon to minimize the effect of the temperature changes. The conductive elements may be mounted on a plurality of individual tiles rather than on an unitary sheet covering an entire wafer to minimize dimensional changes when the dielectric is released from the support structure.

81 Claims, 17 Drawing Sheets

U.S. PATENT DOCUMENTS

| | | | |
|---|---|---|---|
| 3,842,189 A | 10/1974 | Southgate | 174/52 |
| 3,952,404 A | 4/1976 | Mutunami | 29/589 |
| 4,234,666 A | 11/1980 | Gorsky | 428/573 |
| 4,451,505 A | 5/1984 | Jans | 427/98 |
| 4,520,562 A | 6/1985 | Sado et al. | 29/878 |
| 4,535,219 A | 8/1985 | Silwa, Jr. | 219/121 |
| 4,642,889 A | 2/1987 | Grabbe | 29/840 |
| 4,651,191 A | 3/1987 | Ooue et al. | 257/772 |
| 4,751,199 A | 6/1988 | Phy | 437/209 |
| 4,793,814 A | 12/1988 | Zifcak et al | 439/66 |
| 4,893,172 A | 1/1990 | Mutsumoto et al. | 357/79 |
| 4,937,653 A | 6/1990 | Blonder et al. | 357/68 |
| 5,065,223 A | 11/1991 | Matsuki et al. | 257/692 |
| 5,067,007 A | 11/1991 | Kanji et al. | 357/74 |
| 5,086,337 A | 2/1992 | Noro et al. | 357/79 |
| 5,133,495 A | 7/1992 | Angulas et al. | 228/180.1 |
| 5,148,265 A | 9/1992 | Khandros et al. | 357/80 |
| 5,148,266 A | 9/1992 | Khandros et al. | 357/80 |
| 5,152,695 A | 10/1992 | Grabbe et al. | 439/71 |
| 5,173,055 A | 12/1992 | Grabbe | 439/66 |
| 5,173,574 A | 12/1992 | Kraus | 257/775 |
| 5,177,863 A | 1/1993 | Lam | 257/786 |
| 5,192,716 A | 3/1993 | Jacobs | 351/50 |
| 5,196,268 A | 3/1993 | Fritz | 437/220 |
| 5,197,892 A | 3/1993 | Yoshizawa et al. | 439/91 |
| 5,203,075 A | 4/1993 | Angulas et al. | 29/830 |
| 5,210,939 A | 5/1993 | Mallik et al. | 29/840 |
| 5,221,428 A | 6/1993 | Ohsawa et al. | 437/220 |
| 5,225,633 A | 7/1993 | Wigginton | 257/666 |
| 5,230,144 A | 7/1993 | Ootsuki | 437/220 |
| 5,258,330 A | 11/1993 | Khandros et al. | 437/217 |
| 5,266,520 A | 11/1993 | Cipolla et al. | 437/220 |
| 5,316,788 A | 5/1994 | Dibble et al. | 427/98 |
| 5,346,861 A | 9/1994 | Khandros et al. | 437/209 |
| 5,354,422 A | 10/1994 | Kato et al. | 437/220 |
| 5,376,326 A | 12/1994 | Medney et al. | 264/510 |
| 5,398,863 A | 3/1995 | Grube et al. | 228/106 |
| 5,430,614 A | 7/1995 | Difrancesco | 361/785 |
| 5,432,127 A | 7/1995 | Lamson et al. | 437/220 |
| 5,518,964 A * | 5/1996 | DiStefano et al. | 435/14 |
| 5,525,545 A | 6/1996 | Grube et al. | 437/209 |
| 5,548,091 A | 8/1996 | DiStefano et al. | 174/260 |
| 5,557,501 A | 9/1996 | DiStefano et al. | 361/704 |
| 5,578,286 A | 11/1996 | Martin et al. | 423/593 |
| 5,590,460 A | 1/1997 | DiStefano et al. | 29/830 |
| 5,615,824 A | 4/1997 | Fjelstad et al. | 228/180.1 |
| 5,629,239 A | 5/1997 | DiStefano et al. | 216/14 |
| 5,650,914 A | 7/1997 | DiStefano et al. | 361/704 |
| 5,679,977 A | 10/1997 | Khandros et al. | 257/692 |
| 5,682,061 A | 10/1997 | Khandros et al. | 257/666 |
| 5,688,716 A | 11/1997 | DiStefano et al. | 437/182 |
| 5,763,941 A | 6/1998 | Fjelstad | 257/669 |
| 5,801,441 A * | 9/1998 | DiStefano et al. | 435/14 |
| 5,830,782 A | 11/1998 | Smith et al. | 438/123 |
| 5,859,472 A | 1/1999 | DiStefano et al. | 257/674 |
| 5,913,109 A | 6/1999 | Distefano et al. | 438/117 |
| 5,989,936 A | 11/1999 | Smith et al. | 438/106 |
| 6,104,087 A | 8/2000 | DiStefano et al. | 257/696 |
| 6,117,694 A | 9/2000 | Smith et al. | 438/14 |

FOREIGN PATENT DOCUMENTS

| | | |
|---|---|---|
| GB | 2 142 568 | 1/1985 |
| JP | 61-91939 | 5/1986 |
| JP | 1-155633 | 6/1989 |
| JP | 3-198734 | 8/1991 |
| WO | WO 94/03036 | 2/1994 |
| WO | 97/11588 | 3/1997 |
| WO | 97/39482 | 10/1997 |
| WO | 98/28955 | 7/1998 |
| WO | 98/44564 | 10/1998 |

* cited by examiner

MICROELECTRONIC UNIT FORMING METHODS AND MATERIALS

CROSS-REFERENCE TO RELATED APPLICATIONS

The present application is a continuation-in-part of U.S. patent application Ser. No. 09/267,058, filed Mar. 12, 1999, which in turn claims benefit of U.S. Provisional patent application Ser. No. 60/077,928, filed Mar. 13, 1998, the disclosures of which are incorporated by reference herein. The present application is also a continuation-in-part of U.S. patent application Ser. No. 09/138,858 filed Aug. 24, 1998, which in turn is a divisional of U.S. patent application Ser. No. 08/440,665 filed May 15, 1995 now U.S. Pat. No. 5,801,441 which in turn is a divisional of U.S. patent application Ser. No. 08/271,768 filed Jul. 7, 1994, now U.S. Pat. No. 5,518,964, the disclosures of which are hereby incorporated by reference herein. The present application is also a continuation-in-part of U.S. patent application Ser. No. 09/140,589 filed Aug. 26, 1998, the disclosure of which is also incorporated by reference herein, which in turn claims benefit of U.S. Provisional patent application Ser. No. 60/056,965, filed Aug. 26, 1997, the benefit of which is claimed herein and the disclosure of which is also incorporated by reference herein.

BACKGROUND OF THE INVENTION

The present invention relates to microelectronic packaging and more particularly relates to methods of making connectors and packaged microelectronic components. In various microelectronic devices, it is desirable to provide a connection between two components, which can accommodate relative movement between the components. For example, where a semiconductor chip is mounted to a circuit board, thermal expansion and contraction of the chip and circuit board can cause the contacts on the chip to move relative to the corresponding electrically conductive features of the circuit board. This can occur during service and can also occur during manufacturing operations as, for example, during soldering operations on the circuit board.

As illustrated in certain preferred embodiments of U.S. Pat. No. 5,518,964 ("the '964 patent") movable interconnections between elements such as a semiconductor chip and another element can be provided by first connecting leads between the elements and then moving the elements away from one another so as to bend the leads. For example, a connection component may incorporate a dielectric body and leads extending along a bottom surface of the dielectric body. The leads may have first or fixed ends permanently attached to the dielectric element and connected to electrically conductive features such as terminals, traces or the like on the dielectric body. The leads may also have second ends releasably attached to the dielectric body. The dielectric body, with the leads thereon, may be juxtaposed with the chip and the second ends of the leads may be bonded to contacts on the chip. Following bonding, the dielectric body and chip are moved away from one another, thereby bending the leads. During or after movement, a curable material such as a liquid composition is introduced between the elements. This is cured to form a compliant dielectric layer such as an elastomer or gel surrounding the leads. The resulting packaged semiconductor chip has terminals on the dielectric body connection component which are electrically connected to the contacts on the chip but which can move relative to the chip so as to compensate for thermal effects. For example, the packaged chip may be mounted to a circuit board by solder-bonding the terminals to conductive features on the circuit board. Relative movement between the circuit board and the chip due to thermal effects is taken up in the moveable interconnection provided by the leads and the compliant layer.

Numerous variations of these processes and structures are disclosed in the '964 patent. For example, the package-forming process can be conducted on a wafer scale, so that the numerous semiconductor chips in a unitary wafer are connected to connection components in one sequence of operations. The resulting packaged wafer is then severed so as to provide individual units, each including one or more of the chips and portions of the dielectric body associated therewith. Also, the leads may be formed on the chip or wafer rather than on the dielectric body. In further embodiments, also disclosed in the '964 patent, a connector for use in making connections between two other microelectronic elements is fabricated by a generally similar process. For example, in one embodiment a dielectric body having terminals and leads as discussed above is connected to terminal structures on a temporary sheet. The temporary sheet and dielectric body are moved away from one another so as to bend the leads, and a liquid material is introduced around the leads and cured so as to form a compliant layer between the temporary sheet and the dielectric body. The temporary sheet is then removed, leaving the tip ends of the terminal structures projecting from a surface of the compliant layer. Such a component may be used, for example, by engaging it between two other components. For example, the terminal structures may be engaged with a semiconductor chip, whereas the terminals on the dielectric body may be engaged with a circuit panel or other microelectronic component. Thus, the broad invention taught in the '964 patent offers numerous desirable ways of making electrical interconnections and connectors.

Additional variations and improvements of the processes taught in the '964 patent are disclosed in commonly assigned U.S. Pat. Nos. 5,578,286; 5,830,782; and 5,688,716 and in copending, commonly assigned U.S. patent application Ser. No. 08/690,532, filed Jul. 31, 1996 and Ser. No. 09/271,688, filed Mar. 18, 1999, the disclosures of which are hereby incorporated by reference herein.

SUMMARY OF THE INVENTION

The present application is directed to specific embodiments of the '964 patent process and certain embodiments thereof.

One aspect of the invention provides methods of making a microelectronic assemblies. The methods in accordance with this aspect of the invention desirably include a the steps of providing leads physically connected to a bottom surface of a support, each said lead having a tip end and a terminal end and engaging the support with a microelectronic element as, for example, a chip, a wafer or an assemblage of plural discrete chips, having contacts thereon so that the tip ends of the leads are aligned with the contacts of the microelectronic element. The methods further include bonding the tip ends of the leads to the contacts; and then after such bonding, selectively degrading the connection between the support and the leads at and adjacent the tip ends thereof so as to free the tip ends from the support and leave the terminal ends secured to the support. Preferably, the methods include the further step of moving the support and microelectronic element through a predetermined displacement away from one another after degrading the connection between the tip ends and the support so as to deform said leads towards a vertically-extensive disposition. Optionally, the connection between the terminal ends of the leads and the support may be degraded after the moving step, so as to free the support and allow removal of the support. A flowable material may be introduced around the leads during or after the movement step to form a dielectric layer surrounding said leads.

Where the material connecting the tip ends to the support is radiation-sensitive, the step of selectively degrading the connection may include selectively applying radiation through said support at and adjacent to the tip ends of the leads. Thus, in methods according to this aspect of the invention, there is no need to fabricate precise mechanical features such as frangible connections to hold the leads in place until they can be bonded to the microelectronic element. Instead, the tip ends of the leads are constrained reliably until such constraint is released by selective degradation of the connecting layer.

A related aspect of the invention provides methods of connecting a plurality of leads to one or more microelectronic elements. Methods according to this aspect of the invention desirably include the steps of providing the leads physically connected to a support by a connecting material so that said leads are maintained in position on the support at least partially by the connecting material; juxtaposing the support with the microelectronic element so that the leads are aligned with contacts on the microelectronic element and bonding the leads to the contacts of the microelectronic element. After the bonding step, the connection between the leads and the support is released by degrading the connecting material. The step of degrading the connecting material may include directing radiant energy through the support onto said connecting material. Preferably, the leads are flexible after they are released from the support. As further explained below, certain methods according to this aspect of the invention provide for conversion of constrained, inflexible leads to a flexible state simply by releasing the leads from the support, with or without a further step such as bending the leads.

A further aspect of the invention provides methods of making a packaged microelectronic component. Methods according to this aspect of the invention desirably include the steps of providing a support including a structural layer transparent to radiation in a degradation wavelength band and electrically conductive elements secured to said structural layer by a connecting layer on a bottom surface of said structural layer. The conductive elements are connected to a microelectronic component, and then the conductive elements are released from the structural layer by directing radiation in said degradation wavelength band through said structural layer to degrade the connecting layer. The conductive elements or features provided on the support may include leads as discussed above; individual conductive terminals; or conductive terminals incorporated in subassemblies also including dielectric components. The step of connecting the conductive features carried by the support to a microelectronic component may include providing leads extending between said conductive features and the microelectronic component.

The conductive features may be carried on a sacrificial layer having etching properties different from those of the conductive features such that the sacrificial layer can be etched without destroying the conductive features the sacrificial layer being connected to said structural layer by said connecting layer. To provide such different etching properties, the sacrificial layer may be formed from a material different from the material constituting said conductive features. Alternatively or additionally, the sacrificial layer may be formed from the same material as the conductive features but in a thickness substantially less than the thickness of the conductive features. Thus, degradation of the connecting layer frees the sacrificial layer from the structural layer. The method may further include etching the sacrificial layer to remove it without destroying the conductive features. The sacrificial layer can be used to convey plating or etching currents during formation of the conductive features.

A related aspect of the invention provides a support or mandrel for forming microelectronic elements incorporating a structural layer transparent to radiation in a degradation wavelength band; an electrically conductive sacrificial layer thinner than the structural layer; and a connecting layer securing said sacrificial layer to said structural layer, said connecting layer degradable by radiation in said degradation wavelength band.

Yet another aspect of the invention provides a structure for forming microelectronic assemblies. The structure includes a rigid support having a substantially uniform coefficient of thermal expansion and a plurality of electrically conductive elements connected to said support by a connecting material, said support being transparent to radiation in a band of wavelengths effective to degrade said connecting material. Such a structure can be used, for example, in the methods discussed above. The electrically conductive elements on such structure may include features such as leads and terminals. The element may further include one or more sheetlike dielectric layers, the terminals being exposed at a top face of said dielectric layer facing toward said support.

A still further aspect of the invention provides a method of making a plurality of packaged microelectronic components. The method according to this aspect of the invention includes the steps of providing (i) a temporary support with a plurality of separate dielectric elements thereon, each such dielectric element having electrically conductive features thereon; (ii) a microelectronic unit including a plurality of microelectronic devices, and (iii) a plurality of leads, the leads having first ends connected to conductive features on the dielectric elements and having second ends attached to said microelectronic devices. Once these elements have been provided, the temporary support is at least partially removed so as to separate the dielectric elements from one another. Methods according to this aspect of the invention include the realization that, when a unitary dielectric sheet is connected to a relatively large microelectronic unit such as a unitary semiconductor wafer, the support may constrain the thermal expansion of the sheet so as to suppress differential expansion and contraction during to attachment process. However, when the support is removed, the sheet tends to spring back to its unconstrained size. This tendency is restrained by the wafer, leads and encapsulant. However, this tendency may impose internal stress in the assembly, which may damage or distort the assembly. However, when smaller, individual dielectric sheets, also referred to herein as "tiles" are employed, the internal stresses can be reduced substantially, typically by one or more orders of magnitude. Moreover, because these tiles are present on the support during the steps used to connect the conductive features to the microelectronic device, the support maintains the conductive features in the correct spatial relationship for alignment with the contacts or other conductive features on the microelectronic element.

The connection between the tiles and a microelectronic element such as a wafer may be made by means of leads carried on the bottom surfaces of the tiles or on the top surface of the wafer. Most preferably, the step of providing the temporary support with said dielectric elements includes fabricating said dielectric elements and conductive elements on the temporary support. Provided that the support has a predictable coefficient of thermal expansion, the conductive features can be fabricated in precisely-controlled positions. In this aspect of the invention as well, the temporary support may include features such as a radiation-transmissive structural layer and radiation-degradable connecting layer to permit release of the tiles from the support. The support may also include an etchable sacrificial layer.

A related aspect of the invention provides a component for making packaged microelectronic elements. The component includes a support having a structural layer with a substantially uniform, isotropic coefficient of thermal expansion, and a plurality of separate dielectric elements releasably attached to said support structure, said dielectric elements having conductive features thereon. Desirably, the support is formed from a material transparent to radiation of a predetermined degradation wavelength, and the dielectric elements are secured to the structural layer by a connecting material degradable by radiation in such degradation wavelength band. Merely by way of example, the degradation wavelength band may be in the ultraviolet range, the visible range, or the infrared range, although other wavelengths may be used. The transparent material desirably has a coefficient of thermal expansion of about $6 \times 10^{-6}/°C$. or less, so that the transparent material is CTE-matched to silicon to within a reasonable tolerance A further aspect of the invention provides methods of making microelectronic assemblies. Methods according to this aspect of the invention desirably include the steps of providing a semiconductor element such as a wafer including one or more semiconductor chips, said semiconductor element having contacts on a front surface and forming leads in place on the semiconductor element overlying the front surface, said leads having contact ends connected to the contacts and having tip ends releasably connected to the semiconductor element; then juxtaposing said semiconductor element and leads with a further element such as a support and/or dielectric element having pads thereon, and bonding said tip ends of said leads to said pads. Most preferably, the pads are larger than the contacts of the chip and desirably wider than the ends of the leads connected to the pads. As further discussed below, this aspect of the present invention incorporates the realization that where the leads on the chips are aligned to pads wider than the ends of the leads, the process can operate satisfactorily even with a relatively large alignment tolerance. Typically, the contacts on the chip are disposed at first center-to-center distances from one another and the pads are disposed at second center-to-center distances larger than said first center-to-center distances. As also discussed below, this provides room for the pads to have relatively large diameter.

A related aspect of the invention provides an element for forming microelectronic assemblies. The element desirably includes a rigid support having a substantially uniform coefficient of thermal expansion and a plurality of electrically conductive structures defining pads facing away from said support, the conductive structures being releasably connected to said support, the pads desirably being about 150 $\mu$m to about 400 $\mu$m in diameter.

These and other objects, features and advantages of the invention will be more readily apparent from the detailed description of the preferred embodiments set forth below, taken in conjunction with the accompanying drawings.

DETAILED DESCRIPTION OF THE PREFERRED EMBODIMENTS

Figure 1:
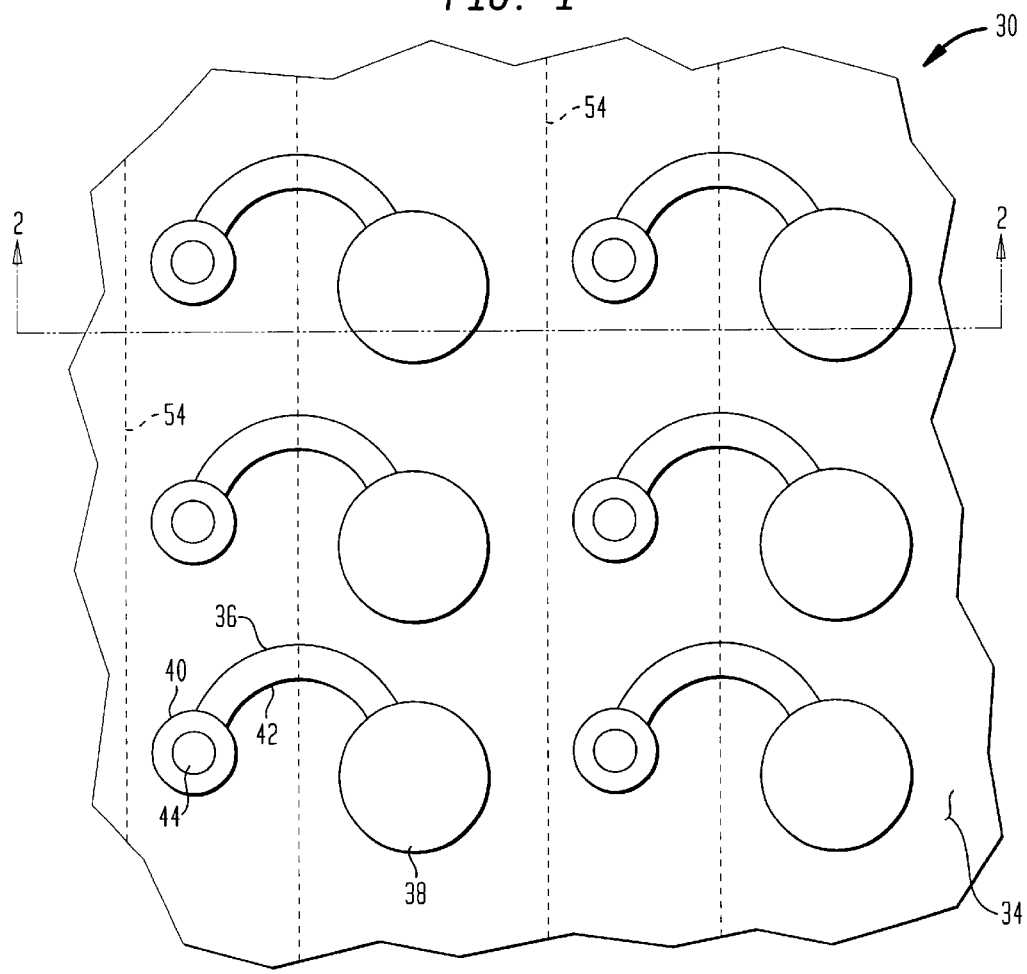
FIG. 1 is a fragmentary, diagrammatic view depicting a portion of a component utilized in one embodiment of the invention.

A method in accordance with one embodiment of the present invention utilizes a support 30 including a structural layer 32 formed from a material having a substantially uniform, isotropic and predictable coefficient of linear thermal expansion ("CTE"). In the process of FIG. 2, the support is to be engaged with a silicon element such as a wafer, as further discussed below. Therefore, the coefficient thermal expansion of structural layer 32 preferably is close to the coefficient of thermal expansion of silicon, i.e., the CTE of structural layer 32 desirably is less than about $6\times10^{-6}/°C$. and more preferably about 1.5 to about $6\times10^{-6}/°C$., most preferably between $2\times10^{-6}/°C$. and $4\times10^{-6}/°C$. Unless otherwise indicated, CTE values set forth in this disclosure are values at about room temperature (20° C.). Also, in the process of FIGS. 1–2, radiant energy is to be directed through the structural layer 32 as further discussed below. Accordingly, structural layer 32 is formed from a material which is transparent to such radiation. Particularly preferred transparent structural materials include glasses, quartz and silicon.

Support 30 further includes a connecting layer 34 formed from a polymeric material which is degradable by exposure to radiation in a predetermined degradation wavelength band. The thickness of connecting layer 34 is greatly exaggerated in FIG. 2 for clarity of illustration. In practice, connecting layer 34 desirably is as thin as practicable. For example, connecting layer 34 may be formed from an ultraviolet-degradable adhesive or other ultraviolet-degradable polymer. Some suitable ultraviolet-degradable adhesives are sold under the designations "Adwill D-570M"; "Adwill D-628"; "Adwill D-650" and "Adwill D-675" as UV-curable dicing tape by the LINTEC Corporation of Tokyo, Japan.

A set of conductive features including leads 36 is provided on the bottom surface of the support, i.e., on the surface of the support covered by the connecting layer 34. Terms such as "bottom"; "top"; "upwardly"; and "downwardly" are used in this disclosure as referencing to the frame of reference of the components themselves, and need not have any relation to the gravitational frame of reference. Each lead has a first end 38, a second end 40 and an elongated portion 42 extending between these ends. In the condition illustrated in FIGS. 1 and 2, the leads are generally planar and the elongated portion 42 of each lead is curved in the plane of the lead. The leads are desirably formed from metals such as one or more metals selected from the group consisting of copper, copper-bearing alloys, gold and gold-bearing alloys. The dimensions of the leads will vary with the application. However, for components to be connected to semiconductor chips, the leads typically are about 250–1000 $\mu$m long from first end 38 to second end 40, about 15–75 $\mu$m wide, and about 5–25 $\mu$m thick in the vertical direction perpendicular to the plane of connecting layer 34. Each lead also has a mass of conductive bonding material 44 disposed on its second end. The bonding material masses face away from support 30. Bonding material 44 may be essentially any electrically conductive bonding material as, for example, a solder; a eutectic bonding material; a diffusion bonding material or an electrically conductive polymeric bonding material. The bonding material 34 may also be an anisotropic conductive material such as a polymer filled with electrically conductive particles. Desirably, conductive bumps (not shown) are deposited on chip contacts 50 for protection of the chip contacts and the underlying semiconductor structures from damage during bonding operations. For example, the bumps may include electrolessly deposited zincated nickel with an overcoating of gold.

Leads 36 desirably are formed in place on the bottom surface of the support. For example, a layer of copper or suitable lead-forming method may be bonded to the bottom surface by connecting layer 34 and then selectively etched using conventional masking and etching techniques to leave the leads in place on the bottom surface. Alternatively, the leads may be formed by an additive process as, for example, by depositing a thin layer of a seed material by conventional electroless plating on the connecting layer and then selectively electroplating the lead material onto the seed layer, followed by removal of the masking material and the brief etch to remove the seed layer in areas other than the areas covered by the leads. The conductive features or leads 36 are disposed in a pattern corresponding to the pattern of contacts on a microelectronic unit to be used in the process. In the process of FIGS. 1–4, the microelectronic element is a semiconductor wafer 48 (FIG. 2) having a large number of contacts 50 exposed at a top surface 52 of the wafer.

Support 30 with conductive features or leads 36 thereon is juxtaposed with the microelectronic unit or wafer 48 so that the second ends 40 of the leads are aligned with the contacts 50 of the microelectronic unit or wafer. Such alignment can be performed, for example, using conventional robotic vision systems. The bonding material 44 at the second ends of the leads is activated so as to bond the second ends of the leads to the contacts. For example, where the bonding material is heat-activated bonding material such as a solder, eutectic bonding alloy or diffusion bonding alloy, the components are brought to an elevated temperature. The components may be forced against one another by a pair of heated platens (not shown), so that heat is applied by conduction through the structural layer 32 of the support and through the wafer 48.

The structural layer 32 of support 30 greatly facilitates precise alignment of the lead ends and the contacts in the stages of the process. Because the CTE of the structural layer and hence the CTE of support 30 as a whole is predictable and isotropic, any change in alignment can be predicted in advance and accounted for in the initial placement of the leads. For example, if the CTE of the structural layer is slightly greater than the CTE of wafer 48, and if the lead-forming process is conducted at room temperature whereas the bonding step is conducted at elevated temperatures, the spacing between lead second ends 40 used in the lead forming step may be slightly less than the nominal, room-temperature spacing between contacts 50 on the wafer. When both parts are heated to the bonding temperature, the structural layer will expand to a slightly greater degree than the wafer and hence the spacing between the leads second ends will be matched to the spacing between the contacts 50. Desirably, the structural layer has a uniform CTE close to that of silicon, and thus temperature changes during the process will introduce only minimal changes in alignment between the lead second ends and the contacts on the wafer.

After the second ends of the leads have been bonded to the contacts on the wafer, connecting layer 34 is degraded by applying radiant energy selectively through structural layer 32 in regions 54 aligned with the second ends of the leads and elongated portions 42 of the leads. The wavelength of the radiant energy is within the degradation wavelength band of connecting layer 34. For example, where the bond layer 34 is degradable by ultraviolet radiation, the radiation applied in regions 54 includes ultraviolet radiation. The radiation may be applied selectively by use of an opaque mask 56 having openings 58 aligned with the regions 54 where the radiant energy is to be applied. The radiant energy may be directed nonselectively onto the top surface of mask 56 and blocked by the mask at all locations other than the openings 58. Alternatively, the radiant energy may be applied by selectively directing a beam of radiant energy such as a beam from a laser downwardly onto the top of the structural layer 32, so that the laser beam impinges on the structural layer only in regions 54 where radiant energy is desired.

Figure 2:
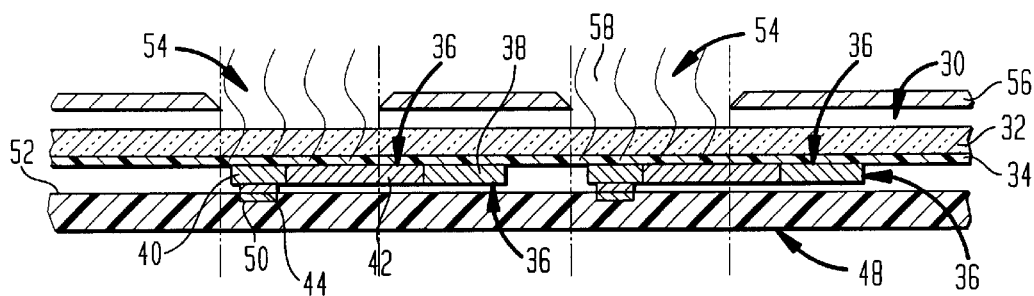
FIG. 2 is a diagrammatic, fragmentary sectional view taken on line 2—2 in FIG. 1, depicting the component of FIG. 1 in conjunction with an additional element during a process according to one embodiment of the invention.

As best appreciated with reference to FIG. 1, regions 54 may be generally in the form of elongated strips extending transverse to the direction of elongation of the leads. For example, a laser beam may be scanned across support 30 in a raster pattern having scanning lines corresponding to the individual strip-like regions 54. The registration of the radiant energy pattern with the leads need not be particularly precise. Moreover, it is not necessary that the radiant energy completely degrade the bond strength in the regions where it is applied. For example, if some portion of the connecting layer at the second end of each lead remains unaffected by the radiant energy, the process will still operate properly, provided that the overall bond strength at the second end is sufficiently degraded that the connection between the second end 40 of the lead and structural layer 32 of support 30 is weaker than the bond between the second end of the lead and the contact 50 of the wafer. As further discussed below, the second ends 40 and elongated portions 42 of the leads are peeled away from the support structure, starting at the second ends of the leads. Therefore, provided that the radiant energy affects the bond at the second end sufficiently for the second end to be peeled away from the support structure, the peeling process will begin at the second end and continue along the length of the lead, even if some or all of the bonds between the support structure and the elongated portions 42 are unaffected by the radiant energy. Also, if some portion of the connecting layer at the first end of each lead is affected by the radiant energy, the system will still operate properly provided that the remaining bond strength at the first end of each lead is sufficient that the first end remains attached to the support layer during the next step of the process. After the connecting layer 34 has been selectively degraded at the second ends of the leads, support 30 and wafer 48 are moved away from one another in a vertical direction V through a preselected distance. For example, the wafer and support may be moved away from one another by the controlled movement of platens engaged with the top surface of support 30 and the bottom surface of wafer 48. During this movement, the support and wafer may also move in a horizontal direction H relative to one another. During this relative movement, the second ends 40 of the leads remain attached to the contacts 50 of the wafer and hence move downwardly relative to the support with the wafer. The first ends 38 of the leads remain attached to support 30. Thus, the relative movement of the components deforms the leads from their generally planar condition (FIG. 2) to the vertically extensive disposition depicted in FIG. 3. During or after such movement, a flowable composition adapted to form a dielectric layer as, for example, a curable liquid composition arranged to form a compliant dielectric layer 60 such as a foam, a gel or an elastomer is introduced between the support 30 and wafer 48. This material is cured to form the dielectric layer intimately surrounding the leads. The process of moving the parts away from one another may be conducted as discussed in the aforementioned '964 patent. Also, the flowable composition may be introduced under a pressure greater than the prevailing atmospheric pressure surrounding the components, and the pressure of the flowable composition may help to impel the wafer and support away from one another. For example, to provide greater assurance against formation of gas bubbles in the dielectric layer, the wafer, the support, and the space between these components may be maintained under a subatmospheric pressure and the flowable composition may be introduced under atmospheric pressure or superatmospheric pressure.

Figure 3:
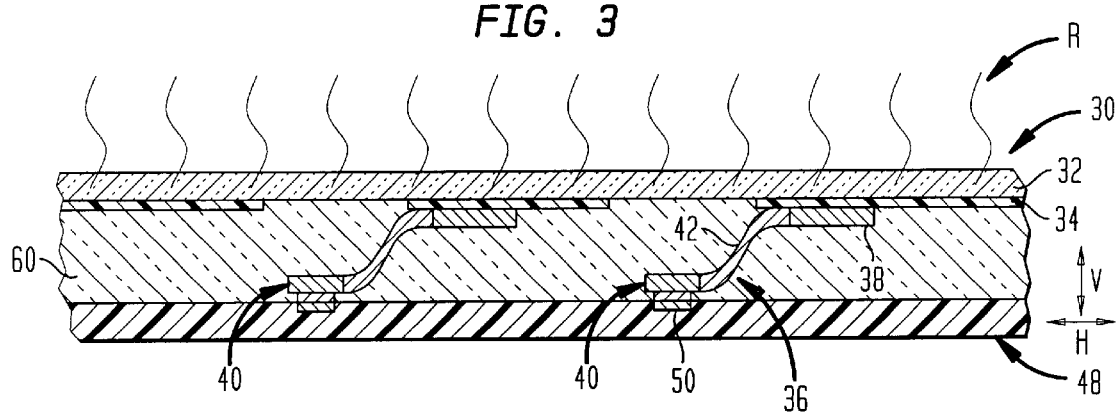
FIGS. 3 and 4 are views similar to FIG. 2 but depicting the component of FIGS. 1 and 2 at later stages in the process.
Figure 4:
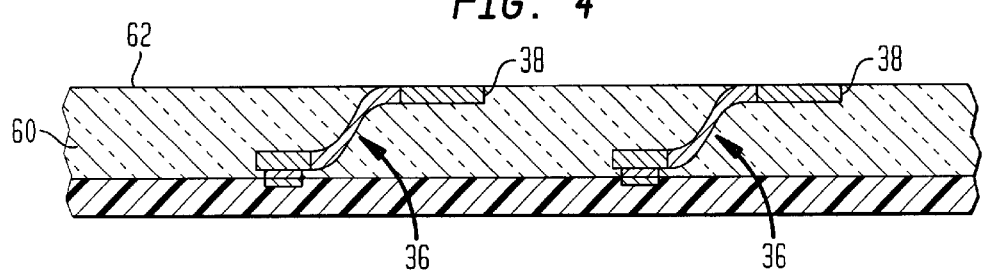
Figure 5A:
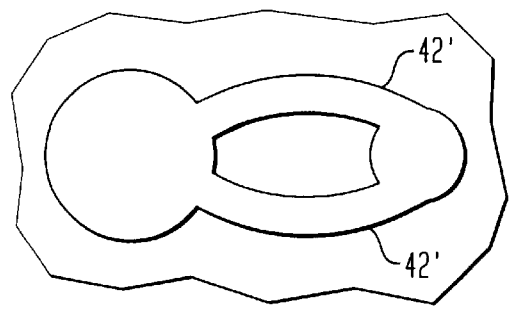
FIGS. 5A, 5B, 6A and 6B are fragmentary, diagrammatic views similar to FIG. 1 but depicting portions of components in accordance with additional embodiments of the invention.
Figure 5B:
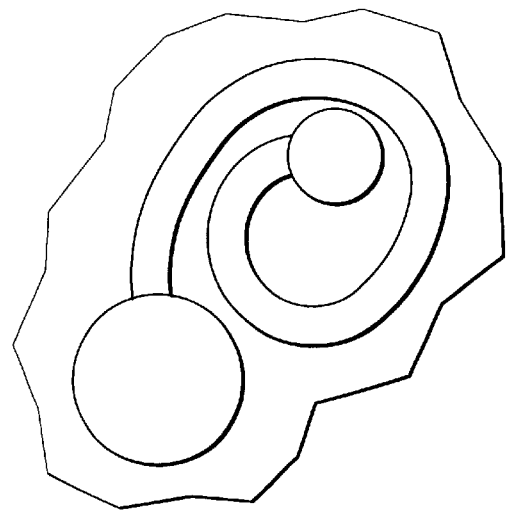

After dielectric layer 60 has been cured, radiation in the degradation wavelength band is applied to at least those areas of the support which were not treated in the prior selective application of the radiant energy, so as to degrade the remaining portions of connecting layer 34 at the first ends of the leads. In this step, the radiant energy may be applied either selectively at those portions of the support aligned with the first ends of the leads or non-selectively over the entire support as depicted in FIG. 3. After degradation of the remaining portions of connecting layer 34, the structural layer 32 of the support is removed, leaving the first ends 36 of the leads as terminals exposed at a surface 62 of the dielectric layer 60 remote from wafer 48, as depicted in FIG. 4. The resulting product can then be severed or "diced", as by conventional wafer-sawing equipment, to form individual units, each including one semiconductor chip with the associated leads 36 and exposed terminals 38. Such a unit or packaged chip can be mounted to a circuit or other circuit panel with the terminal 38 bonded to the circuit panel. As described in greater detail in the '964 patent, relative movement between the chip and the circuit panel caused, for example, by thermal expansion and/or warpage of the components during operation and during manufacturing processes will accommodated by flexure of leads 36. Thus, such relative movement will not impose substantial stresses on the solder or other bonding material used to secure terminals 36 to the circuit panel.

Figure 6A:
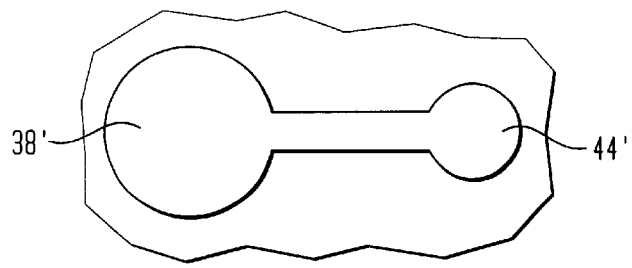
Figure 6B:
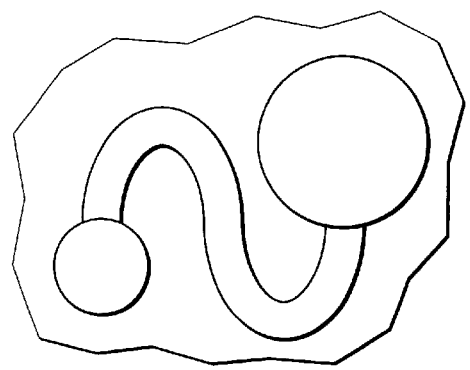

Other lead configurations, such as those illustrated in FIGS. 5A, 5B, 6A, and 6B may be employed. The lead of FIG. 5A, which incorporates two elongated, curved main sections 42 provides a pair of connections extending in parallel between the first and second ends. Leads of this type are discussed further in U.S. Pat. No. 5,859,472, the disclosure of which is hereby incorporated by reference herein. Straight leads as shown in FIG. 6A are also described in certain embodiments of the aforementioned '964 Patent can be employed. Typically, where such straight leads are employed, the support structure 30 and wafer 48 move relative to one another in a horizontal direction so that the second end 44 of the lead moves towards the first end 38 in the horizontal direction while the second end moves away from the first end in the vertical direction. This action is described in greater detail in the aforementioned '964 Patent. Still other lead configurations which can be used in processes according to this aspect of the invention are disclosed in co-pending, commonly assigned U.S. patent application Ser. No. 08/712,855, the disclosure of which is hereby incorporated by reference herein.

A process according to a further embodiment of the invention uses a support 130 with a structural layer 132 and the connecting layer 134 similar to the corresponding elements discussed above with reference to FIGS. 1–4. Support 130 further has a sacrificial metal layer 135 disposed on its bottom surface, i.e. on the surface of connecting layer 134 so that the connecting layer holds the sacrificial layer on the support layer. Here again, the layer thicknesses are greatly exaggerated. Typically, sacrificial layer 135 is a foil about 5 to about 25 $\mu$m thick. Sacrificial layer 135 is formed from an electrically conductive material different from the material used to form the leads. The material of the sacrificial layer desirably can be etched by an enchant which does not substantially attack the material of the leads. For example, where the leads are formed from gold or a gold-bearing alloy, the sacrificial layer may be formed from copper or a copper-bearing alloy where the leads are formed from copper or copper alloy, the sacrificial layer may be formed from aluminum or an aluminum alloy.

Figure 7:
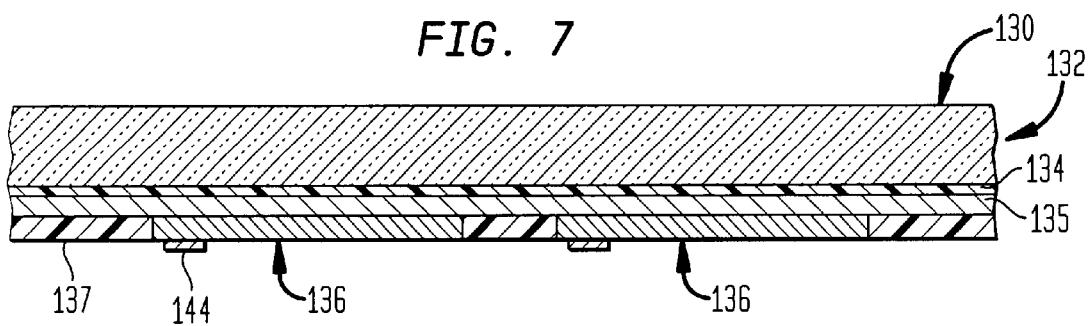
FIG. 7 is a fragmentary, diagrammatic sectional view depicting portions of a component in accordance with a further embodiment of the invention.
Figure 8:
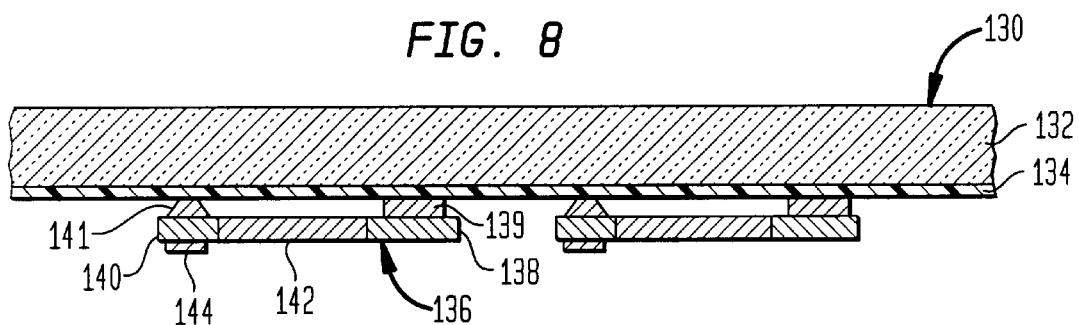
FIGS. 8, 9 and 10 are views similar to FIG. 7 but depicting the component in progressively later stages of a process according to a further embodiment of the invention.
Figure 9:
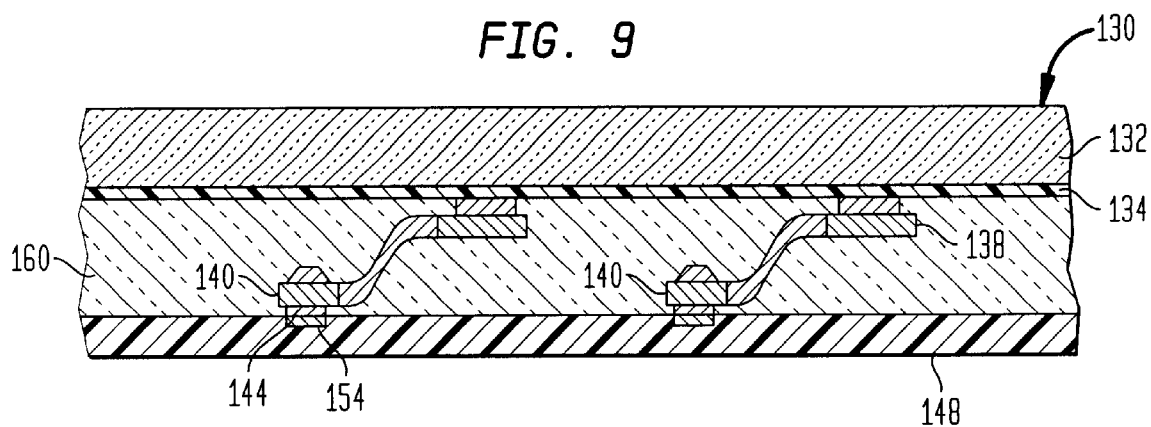
Figure 10:
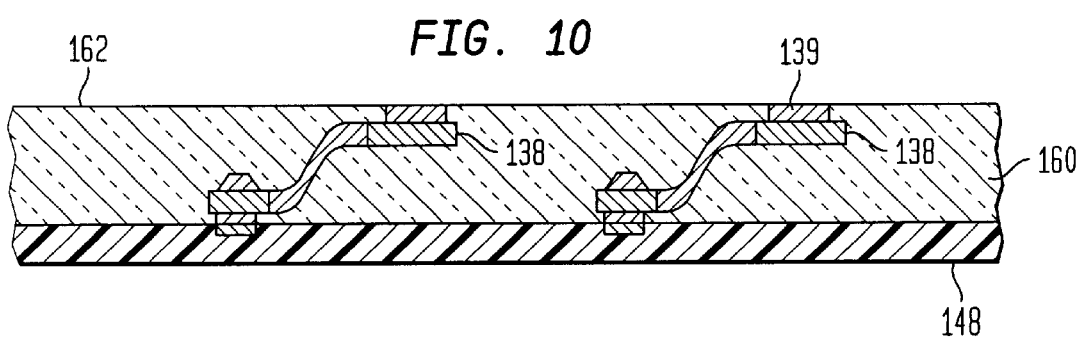

As illustrated in FIG. 7, the leads may be formed in a place by an additive plating process wherein a masking layer 137 such as a conventional photoresist is deposited on the surface of sacrificial layer 135 leaving openings. The leads 136 are plated onto the sacrificial layer in such openings. Alternatively, a layer of lead-forming material may be provided on the surface of the sacrificial layer and the leads may be formed by a subtractive etching process. In such a subtractive process, the masking material is applied over the lead-forming material in the areas where the leads are to be formed. In either case, the sacrificial layer 135 may be used to conduct plating or etching currents. The sacrificial layer thus simplifies fabrication of the leads. Again, a conductive bonding material 144 may be deposited at the second ends of the leads.

In the next stage of the process, the masking material is removed and the bottom surface of the support, with the leads and sacrificial layer thereon, is exposed to an enchant which attacks the sacrificial layer but which does not substantially attack the leads. Areas of the sacrificial layer which are not covered by the leads 136 are removed rapidly. Also, in areas of the sacrificial layer covered by the relatively narrow elongated main portions 144 of the leads, the sacrificial layer is removed from between the lead and the connecting layer 134. The first end 138 of each lead has a large diameter so that it effectively shields a portion of the sacrificial layer. Although the sacrificial layer is attacked at the edges of the first end 138, the etching process is stopped before the sacrificial layer is completely removed at the first end. Thus, a connector 139 formed from the sacrificial layer material remains at the first end of each lead. Similarly, at the second end of 140 of each lead, a small connector or button 141 remains when the etching process is terminated. Buttons 141 are substantially smaller than connectors 139. The buttons provide only a weak connection between the second end of each lead and the connecting layer 134; the strength of the connection is directly related to the surface area of the connecting layer covered by the residual portions of the sacrificial layer in buttons 141. The surface areas covered by buttons 141 are substantially smaller than the surface areas covered by connectors 139. Thus, after this process, the second end 140 of each lead is releasably connected to the connecting layer 134 whereas the first end 138 remains strongly attached to the connecting layer.

In the next stage of the process, the support structure 130, with leads thereon is juxtaposed with a wafer 148. The second ends 140 of the leads are aligned with the contacts 150 of the wafer and bonded thereto by means of the bonding material 144. The support structure and wafer are then moved away from one another and a curable material is injected to form a dielectric layer 160 in the same manner as discussed above with reference to FIG. 3. Buttons 141 break away from connecting layer 134. In a variant of this process, the connecting layer can be degraded selectively at the second ends of the leads as discussed above. After curing of the dielectric layer, connecting layer 134 is degraded non-selectively, over the entire area of support structure 130. Such non-selective degradation may be accomplished by exposure to radiant energy as discussed above. Alternatively or additionally, the connecting layer 134 may be degraded by exposure to heat or chemical agents. Suitable heat degradable materials for formation of a connecting layer are sold by the Nitto Denko Company of Japan. Where the bonding material is heat degradable, the degradation temperature desirably is above the temperatures attained in the stages prior to movement of the support structure and wafer away from one another. Stated another way, the connecting layer material should remain effective at least for long enough to pull the lead first ends upwardly relative to the second ends 140. Thus, connecting layer 134 desirably has a degradation temperature above the temperature used to activate the bonding material 144 at the second ends of the leads. Degradation of the connecting layer may occur simultaneously with or after curing of dielectric layer 160. Alternatively or additionally, connecting layer 134 may be chemically degraded by the material used to form dielectric layer 160. For example, the material of the connecting layer may be soluble in the curable composition used to form the dielectric layer. Also, the material used to form the dielectric layer may carry a catalyst which initiates decomposition of the connecting layer.

Where the connecting layer is degraded by a phenomenon other than an application of radiant energy through structural layer 132, the structural layer may be opaque. Suitable opaque support materials having the desired coefficient of thermal expansion for use with a silicon wafer include molybdenum and Invar. The aforementioned preferred radiation-transmissive support layer materials, such as glasses, silicon, and quartz can also be used even if the radiation transmissive properties of these materials are not required.

In a further alternative, connecting layer 134 may be degraded by radiant energy such as infrared energy transmitted through wafer 148, either before or after introduction of the material used to form the dielectric layer 160. This approach is less preferred inasmuch as metallic or other opaque structures within the wafer can block transmission of radiant energy. Also, the radiant energy must be applied without overheating the internal structures of the wafer.

After degradation of connecting layer 134, structural layer 132 is removed, leaving connectors 139 as exposed terminals at the surface 162 of layer 160 remote from wafer 148. Here again, the wafer and dielectric layer 160 may be diced to form individual units. In a further alternative, connectors 139 may be removed by exposing surface 162 to an enchant adapted to dissolve the material of the sacrificial layer. For example, where connectors 139 are formed from aluminum left from an aluminum sacrificial layer 135, an alkaline etch can be used to remove the connectors. This leaves the first ends 138 of the leads as terminals exposed at surface 162 but slightly recessed beneath the surface. These terminals, however are still accessible for making further electrical contact. For example, solder balls can be deposited on such recessed contacts 138. Such solder balls can be engaged with a circuit panel.

Figure 11:
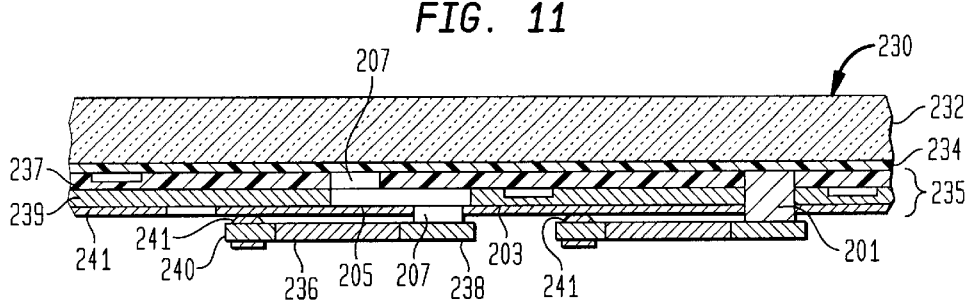
FIG. 11 is a fragmentary diagrammatic sectional view of depicting a component according to yet another embodiment of the invention.

In a method according to a further embodiment, a support structure 230 (FIG. 11) incorporates a structural layer 232 and connecting layer 234 similar to the corresponding components of the support structure discussed above. A multi-layer structure 235 is disposed on the bottom surface of the support, i.e., on the surface of connecting layer 234 facing away from structural layer 232. The multi-layer structure includes several dielectric layers 237, 239, and 241 as well as conductive elements such as through vias 201, traces 203 extending in horizontal directions along or within the layers, and more complex conductive structures such as conjoined traces 205 and vias 207.

The conductive elements in the multi-layer structure 235 include leads 236 having first ends 238 permanently connected to the dielectric layers and second ends 240 releasably connected to the dielectric layers. For example, the leads may be formed on the bottom dielectric layer 241 and that layer may be etch so as to remove dielectric material in the regions not covered by the leads and also remove dielectric material from beneath the leads. Removal of material from the bottom dielectric layer leaves small polymeric connecting elements 241 at the second ends of the leads. These small connecting elements are breakable and hence the second ends of the leads are releasably connected to the remainder of the structure 235. The first ends of the leads are permanently attached to the structure; such as by vias or other conductive features extending into the structure. Etching of polymeric layers may be performed, for example, using an oxidizing plasma. Processes for plasma etching to form releasable attachments between the leads and polymeric structures are discussed in greater detail in co-pending, commonly assigned U.S. patent application Ser. Nos. 09/020,750 and 09/195,371, the disclosures of which are hereby incorporated by reference herein.

The dielectric layers can be formed in place on the surface of the support structure by processes such as electrophoretic deposition or spin-coating on the surface of the dielectric layer. Vias may be formed in such a deposited layers by conventional processes such as laser ablation or etching. The metallic conductive structures can be provided using additive processes such plating and/or subtractive processes such as etching. Temporary metallic layers may be provided to convey plating or etching currents. Other conductive structures may be provided in multi-layer structures 235, such as electrically conductive ground and/or power planes. Temporary connections may be provided for conveying plating or etching currents by forming temporary conductive features (not shown) in areas of the structure will later be removed from the finished product.

Alternatively, the multi-layer structure 235 may be found separately from the structural layer and laminated thereto using bond layer 234 as laminating adhesive. Formation of the multi-layer structure in place on support 232 is preferred, however, because the support controls the position of the various features during the formation process. Stated another way, when the features are formed in place on the support, they can be positioned with great accuracy because the expansion and contraction of the dielectric layers are controlled by the support during the process.

Figure 12:
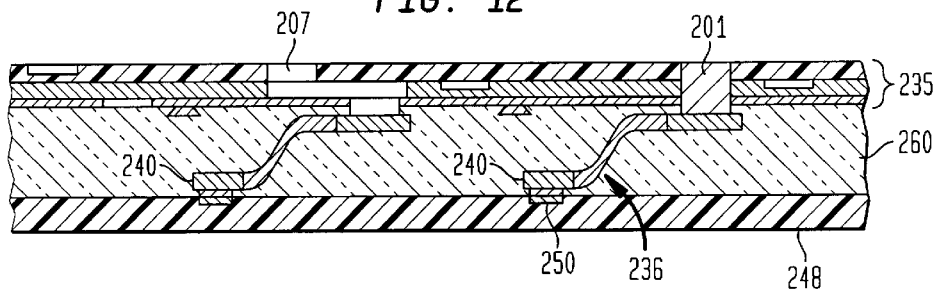
FIG. 12 is a view similar to FIG. 11 depicting the component of FIG. 11 in conjunction with a further element during a later stage of the process according to yet another embodiment of the invention.

In a process according to a further embodiment of the invention, support 232 is juxtaposed with a wafer 248 or other microelectronic element so as to align the second ends 240 of the leads with the contacts 250 of the wafer. The second ends of the leads are bonded to the contacts and the support structure is moved away from the wafer in the manner described above. The connecting elements 241 peel away from the leads or break during this process. The dielectric layer 260 is formed by introduction of a flowable material and curing of such material as described above. After the support structure has been moved away from the wafer, connecting layer 234 (FIG. 11) is degraded, as by application of radiant energy through support layer 232 or by application of heat so as to release the structural layer. The structural layer of the support is removed from the multi-layer structure 235, leaving the assembly as illustrated in FIG. 12. Here again, the assembly can be diced to form individual units, each including one or more chips and a portion of the multi-layer structure 235 electrically connected thereto by the vertically extensive leads 236.

Electrically conductive features such as vias 201 and 207 form terminals exposed to the top surface of the dielectric structure, i.e., to the surface facing toward support layer 232. The terminals or vias 201, 207 provided in the multi-layer dielectric structure can be used as terminals for mounting each unit to a circuit board or other component. As described in greater detail in the aforementioned '964 patent and as discussed above herein, the flexible, vertically extensive leads 236 allow movement of the terminals 201, 207 relative to the contacts 250 on the wafer or chip and hence provide compensation for differential thermal expansion and similar effects during manufacture or service.

Figure 13:
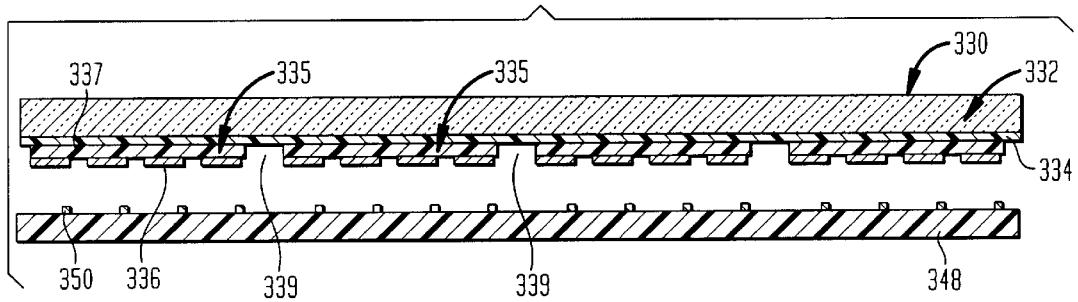
FIG. 13 is a diagrammatic elevational view depicting components according to a further embodiment of the invention.

As depicted in FIG. 13, a support structure 330 may include a unitary structural layer 332 having horizontal dimensions (to the left and the right as seen in FIG. 13) comparable to the corresponding dimensions of a wafer 348. Structural layer 332 may be similar to the structural layers discussed above. The support further includes a connecting layer 334 on the bottom surface of the structural layer. A set of individual elements or tiles 335 is disposed on the bottom surface of the support. Each tile desirably includes one or more dielectric layers as well as conductive features. For example, each tile may be a multi-layer structure similar to that discussed above with reference to FIGS. 11 and 12 or else may be a simple, single-dielectric layer structure. In the particular embodiment illustrated in FIG. 13, the conductive features include flexible leads 336 extending along the bottom surface of the dielectric element 337. The individual tiles are physically connected to one another only by support by 330. Thus, there are channels 339 extending between the tiles 335. However, the tiles, and particularly the conductive features such as leads 336 of the tiles, are disposed in precise relationship with one another so that the spacings between conductive features correspond to the spacings between contacts 350 of wafer 348. In a particularly preferred arrangement, tiles 337 are formed in place on the bottom surface of the support, i.e., on connecting layer 334. For example, all of the tiles may be formed as a unitary element including, for example, unitary dielectric layers and/or unitary conductive layers or tracers extending among all of the tiles. These features can then be severed by laser-ablating the unitary layers and/or etching them to form channels 339. Other removal processes such as mechanical cutting, abrasion or water-jet machining may be used to form channels 339. As discussed above with reference to FIG. 11, conductive features can be formed using temporary conductive elements in regions of the structure which are later removed. Such temporary conductive elements may be provided in the regions which are removed to form channels 339.

Figure 14:
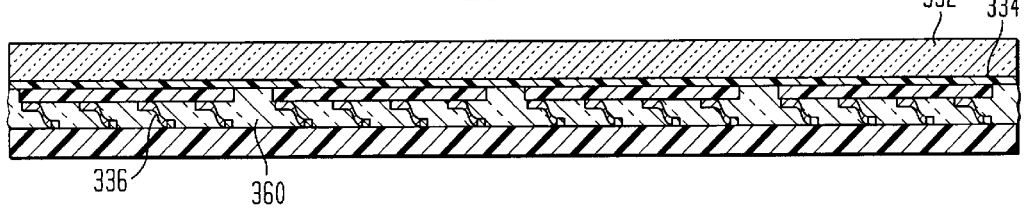
FIGS. 14 and 15 are views similar to FIG. 13 but depicting the components of FIG. 13 during progressively later stages of the same process.

Support structure 332, with tiles thereon 335 is engaged with a wafer 348 in substantially the maimer discussed above, so as to bond the ends of leads 336 to contacts 350. The support structure is moved away from the wafer so as to deform leads 336 into a vertically extensive disposition (FIG. 14). Here again, a flowable material such as a liquid composition is introduced between the support structure and the wafer and cured to form a dielectric layer, desirably a compliant dielectric layer 360 such as a gel, foam or elastomer. During or after curing of dielectric layer 360, connecting layer 334 is degraded, as by application of radiant energy, heat or chemical action so that support structural layer 332 can be removed. The resulting structure (FIG. 15) has the individual tiles attached to the wafer by the compliant dielectric layer 360 and by flexible, vertically extensive leads 336. The structure can be diced as by cutting along lines 353 between the tiles so as to provide individual units, each including one or more chips and a single tile or a few tiles.

The use of separate, individual tiles provides significant benefits, particularly where process steps such as lead-bonding occur at temperatures significantly different from room temperature and/or significantly different from temperatures used in other steps of the process. The dielectric layers and conductive features typically have coefficients of thermal expansion substantially greater than the coefficient of thermal expansion of wafer 348. For example, a typical polyimide/copper structure has a CTE of about $17 \times 10^{-6}/°C$., whereas the wafer typically has a CTE of about $3 \times 10^{-6}/°C$. Where a unitary polyimide/copper structure extends over an entire wafer of about 200–300 mm diameter, the differential thermal expansion between the polyimide/copper structure and the wafer through a temperature difference of about 200° C. may be on the order of 0.25–1 mm. As mentioned above, the support structure, and particularly the rigid structural layer 332 controls expansion and contraction of the polyimide/copper structure during the bonding process. However, when the support structure is removed, the polyimide/copper structure tends to spring back to its normal, unconstrained size. Thus, the conductive features on the polyimide/copper structure tend to move relative to the contacts of the wafer of by 0.25 mm–1 mm or more.

While the flexible leads and compliant layer provided in accordance with the preferred embodiments of this invention can provide more than enough compensation for the degree of differential expansion and contraction encountered in an assembly the size of a single chip or a few chips, they typically are not designed to permit 0.25 mm–1 mm or more of relative movement. Therefore, internal stresses can be imposed within the assembly when an assembly incorporating a large, unitary, wafer sized polyamide/copper structure is released from the support structure. Typically, the compliant layer is placed in shear and some of the leads are placed in tension. The wafer is placed under stress which tends to warp the wafer, and hence the entire assembly, out of planarity. By contrast, where the support structure bears individual tiles, tiles are free to move relative to one another when the support structure is removed. Thus, differential expansion and contraction effects accumulate over only the extent of a single tile. The maximum relative movement upon removal of the support corresponds to the differential expansion or contraction over the extent of a single tile, and not over the extent of a whole wafer. Typically, each tile is about the size of a single chip or a few chips and has horizontal dimensions on the order of about 10–30 mm. Thus, the effects of differential expansion and contraction are dramatically reduced relative to the case where a unitary dielectric/conductive assembly is employed over the entire wafer.

A method according to yet another embodiment of the invention uses a support structure 430 having an opaque structural layer 432 such as a layer of solid molybdenum or other metal having CTE matched to silicon, i.e., having a CTE less than about $6 \times 10^{-6}/°C$. A set of tiles 435 similar to the tiles discussed above with reference to FIGS. 13–15 is provided on a bottom surface of support 430. The tiles are connected to structural layer 432 by a heat-degradable bond layer 434. Also, leads 436 are formed on the top surface of wafer 428 rather than on the tiles. Here again, each lead has a first end 438 and a second end 440. The second ends of the leads are permanently connected to contacts 450 of the wafer. The first ends of the leads are movable relative to the wafer. In the bonding process, the first ends of the leads are aligned with and bonded to conductive features such as contacts 451 on the tiles. Here again, the connected leads extend between the first element or support structure 432 and tiles and the second element or wafer 428. Once again, the elements are moved away from one another so as to deform the leads towards a vertically extensive disposition. A dielectric layer is formed around the leads as by introducing a curable composition. The support structure 430 is then removed by degrading bond layer 434.

Figure 15:
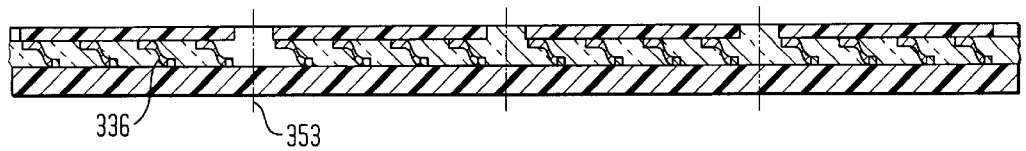
Figure 16:
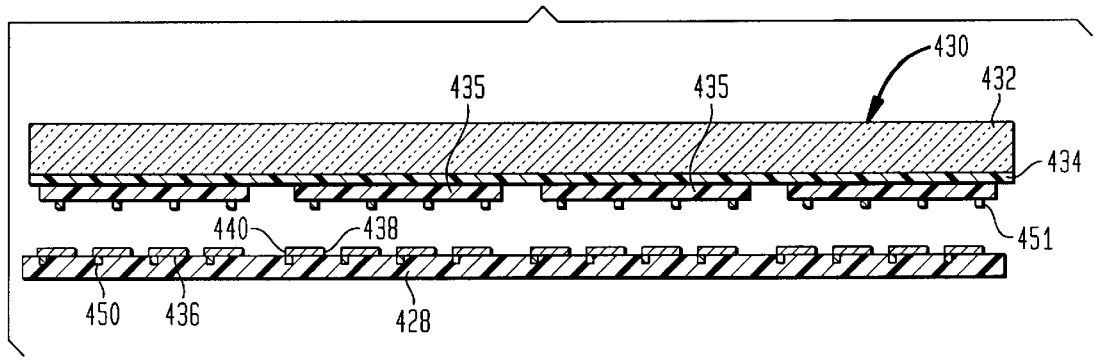
FIG. 16 is a view similar to FIG. 13 but depicting components in accordance with a further embodiment of the invention.
Figure 17:
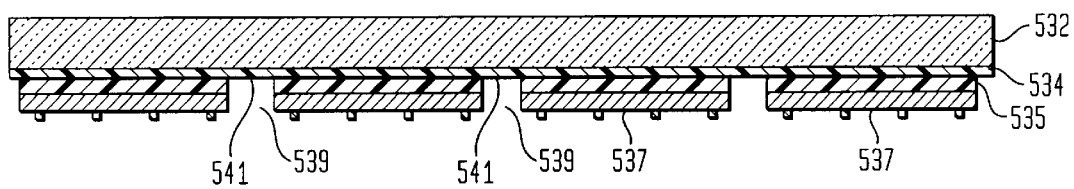
FIG. 17 is a fragmentary diagrammatic sectional view depicting a component according to yet another embodiment of the invention.

In yet another alternative, the support structure may include a degradable bond layer 534 on a structural layer 532 CTE matched to the wafer and may also include an etchable sacrificial layer 535 disposed between the bond layer and the tiles 537 (FIG. 17). After connection with the leads and forming the leads, bond layer 534 is released and the etchable sacrificial layer 535 is removed by etching. Sacrificial layer 535 may be a thin foil as discussed above so as to minimize the time required for etching. Also, because the sacrificial layer is substantially thinner than the structural layer, the structural layer controls thermal expansion and contraction of the support as a whole. Desirably, the structural layer is at least 5 times, and more desirably at least 10 times, as thick as the sacrificial layer. The sacrificial layer may be subdivided into individual pieces, each associated with one tile, as by forming channels 541 in alignment with channels 539 between the tiles. Channels 541 typically are formed after the sacrificial layer has been used to convey plating or etching currents. This arrangement provides the benefits associated with individual tiles as discussed above. The same benefits can be obtained even where the tiles are not completely separated from one another. Thus, the channels 339 (FIGS. 13 and 14) and/or channels 539 of FIG. 17 need not be continuous. Instead, such channels may be interrupted by connectors integral with the tiles extending between tiles. If these connectors are flexible enough to allow the tiles to move relative to one another, such relative movement of the tiles will still relieve stresses when the tiles are released from the support. Likewise, flexible connectors may extend between individual pieces of the sacrificial layer, across channels 541. The connectors may be severed when the wafer is severed along cut lines 353 (FIG. 15).

Similar benefits can be obtained even where the tiles are not completely separated from one another. Thus, the channels 339 (FIGS. 13 and 14) may not be continuous but instead may be interrupted by bridge elements integral with the tiles extending between tiles. If these bridge elements are flexible enough to allow the tiles to move relative to one another, such relative movement of the tiles will still relieve stresses when the tiles are released from the support. The connectors may be severed when the wafer is diced.

Figure 18:
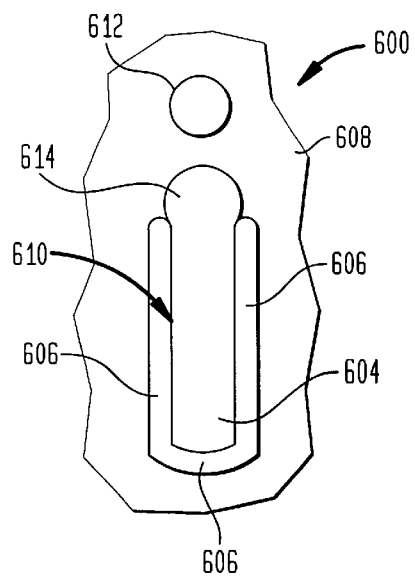
FIG. 18 is a fragmentary diagrammatic plan view depicting portions of a component according to yet another embodiment of the invention.
Figure 19:
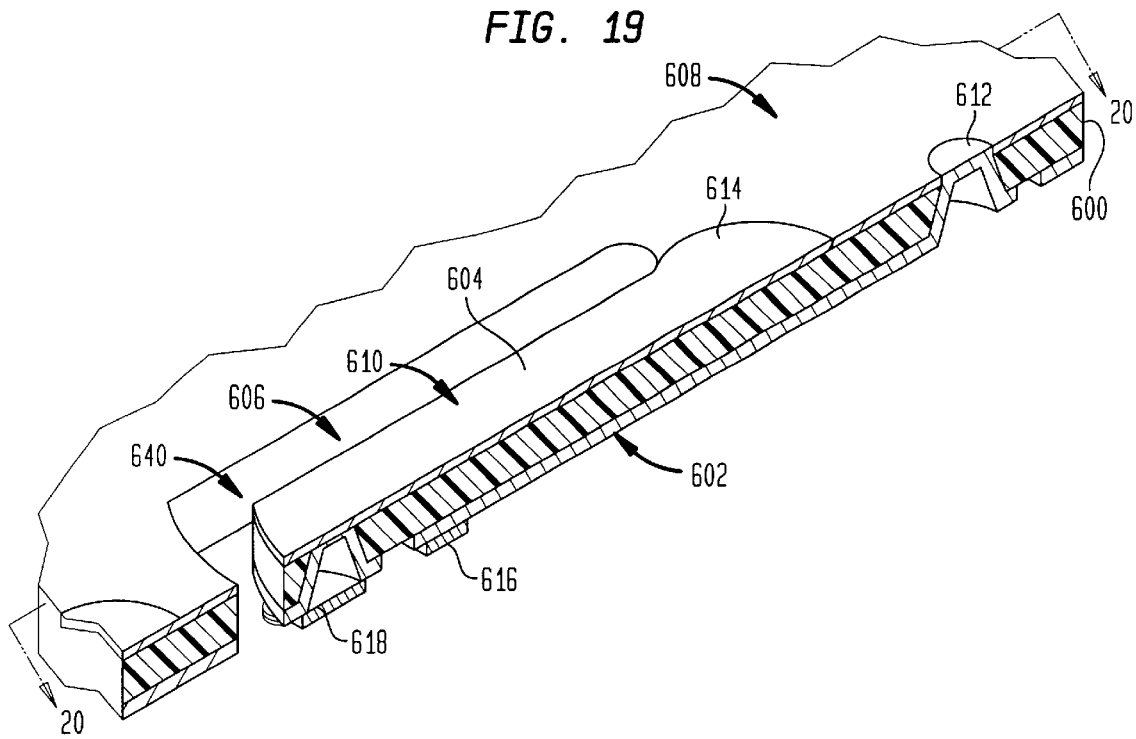
FIG. 19 is a fragmentary perspective cutaway view of the component shown in FIG. 18.

As described in greater detail in the aforementioned U.S. patent application Ser. No. 09/140,589, leads can be made by forming gaps in a layer of material so as to form elongated lead regions partially surrounded by such gaps. For example, as seen in FIGS. 18 and 19, a sheet including a polymeric layer 600 is provided with metallic strips 602 on a bottom surface and strips 604 on a top surface overlying strips 602. Gaps 606 extend around those portions of polymeric layer 600 carrying strips 604 and 602, thus subdividing the polymeric sheet 600 into a main region 608 and a set of lead regions 610. Each lead region 610 forms a lead which can be bent or otherwise deformed independently of the other leads. Each such lead includes a first conductor 602 on the bottom surface and a second conductor 604 on the top surface. As best seen in FIG. 19, the main portion 608 of the sheet carries a pair of terminals associated with each such lead, including a first terminal 612 connected to the first conductor 602 and a second terminal 614 connected to the second conductor. These terminals are accessible at the top surface of the sheet. Bonding material masses 616 and 618 are provided adjacent the second or tip end of each lead. Such a structure may be formed in place on the bottom surface of a support structure incorporating a structural layer 632 and connecting layer 634 similar to the layers discussed above.

Figure 21:
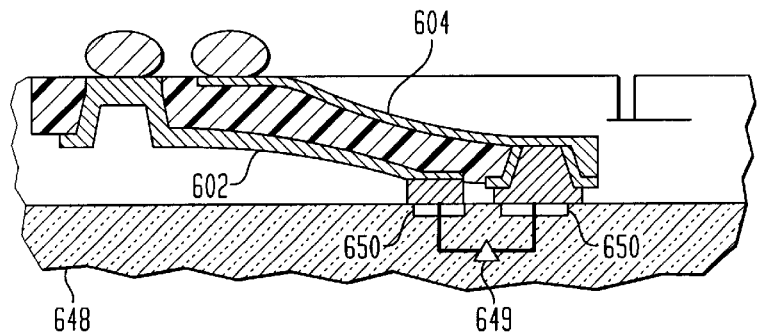
FIG. 21 is a view similar to FIG. 20 but depicting the component at a later stage of the process.

In a process according to an embodiment of the present invention, the sheet is juxtaposed with a wafer 648 and the bonding material masses are connected to contacts 650 on the wafer. Connecting layer 634 is then selectively degraded in regions adjacent the tip ends 640 of the leads and the support structure 630 is moved away from the wafer so as to deform the leads as depicted in FIG. 21. Once again, a curable material is injected around the leads. The dual conductors 602 and 604 provide a circuit path having known, controlled impedance. As explained in greater detail in the aforementioned U.S. patent application Ser. No. 09/140,589; and in copending, commonly assigned U.S. patent application Ser. No. 08/715,571 filed Sep. 19, 1996 and Ser. No. 09/020,754 filed Feb. 9, 1998 and in PCT International Publication WO 97/11588, the disclosures of which are hereby incorporated by reference herein, such a controlled impedance signal path may incorporate a signal conductor and a ground plane or ground conductor extending generally parallel to one another, or else may include a set of two or more signal conductors extending parallel to one another. As discussed in detail in these applications, a circuit 649 within the chip or wafer 648 may be arranged to transmit oppositely-directed pulses on a set of adjacent contacts 650. The conductors of a multi-conductor lead may be connected to the contacts of such a set.

As also described in these applications, arrangements incorporating more than two conductors on a lead may be employed as, for example, a lead which incorporates three conductors such as a reference conductor and two opposite signal conductors conveying oppositely-directed pulses. As also described in these applications, multi-conductor signal paths and strip lines may extend along the dielectric layers. For example, the main region 608 of the dielectric layer may be provided with one or more layers of signal conductors. These interconnections can provide controlled-impedance signal paths between multiple components attached to the dielectric element. Also, as described in International Publication WO 98/44564, the disclosure of which is also incorporated by reference herein, such interconnections may be used to provide controlled impedance signal paths between and among contacts of a single semiconductor chip. All of these arrangements may be implemented in accordance with the present invention.

Figure 20:
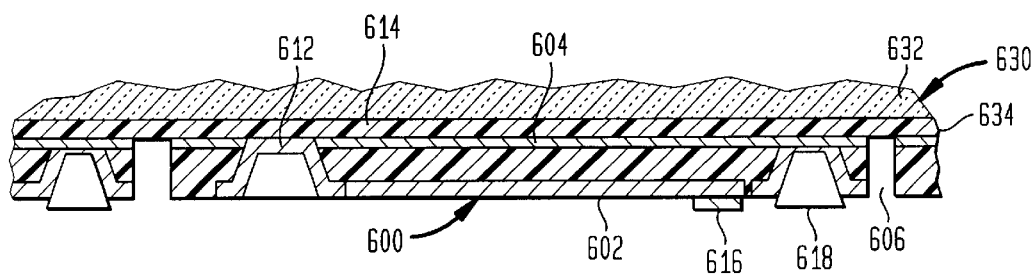
FIG. 20 is a diagrammatic sectional view on line 20—20 in FIG. 19, depicting the component of FIGS. 18–19 in conjunction with a further element during a process according to the invention.

Multi-conductor leads may also be incorporated in methods and components according to the other embodiments discussed above. Thus, the leads used in the embodiments discussed above with reference to FIGS. 1–17 can be fabricated as multi-conductor leads with dielectric elements in between the conductors. Conversely, a dielectric sheet of the type used in the embodiment of FIGS. 18–21 can be fabricated as a plurality of tiles as described above with reference to FIGS. 13–18.

Figure 22:
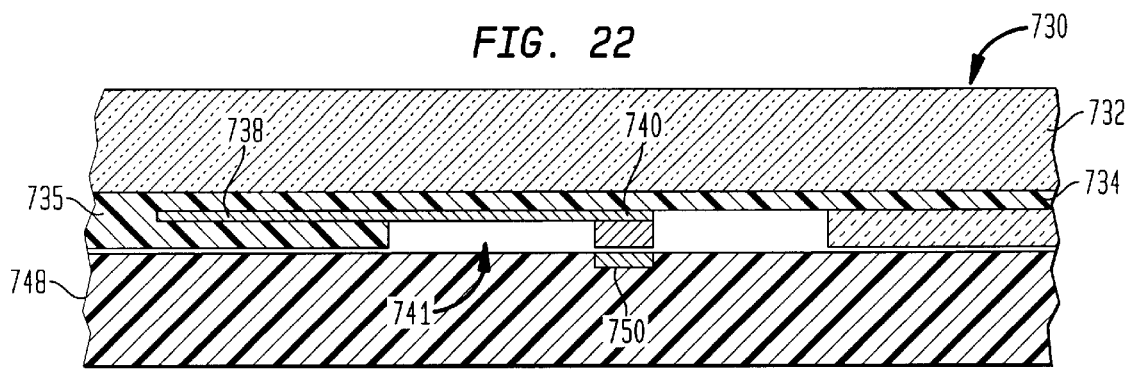
FIG. 22 is a diagrammatic, fragmentary sectional view depicting components according to a further embodiment of the invention in a further process of the invention.
Figure 23:
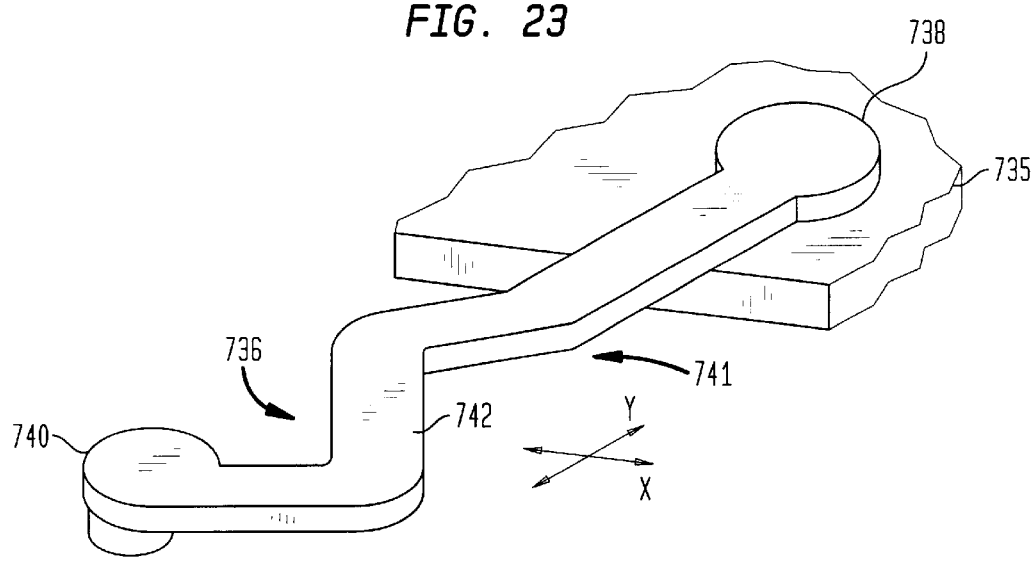
FIG. 23 is a fragmentary perspective view of a component shown in FIG. 22.

In the embodiments discussed above, the leads are rendered more flexible by bending them into a vertically extensive disposition, as by moving the support and the wafer or chips away from one another. However, such a step may be omitted in certain cases. For example, a support structure including a structural layer 732 and connecting layer 734 (FIG. 22) carries a component incorporating a dielectric element and a set of leads 736. Each lead has a terminal at its fixed or first end 738 on the dielectric layer and a second end 740 projecting from the dielectric layer. For example, the second ends of the leads may project over apertures 741 in the dielectric layer or else may project beyond the periphery of the dielectric layer. The leads have elongated main portions 742. The main portions 742 are curved in the horizontal directions, parallel to the plane of sheet 735. The particular zigzag shape illustrated in FIG. 23 is merely exemplary. The shapes shown in FIGS. 5A, 5B and 6B, and other shapes incorporating curved main portions can be employed. These curved main portions allow freedom of movement of the second ends 740 relative to the first ends 738 in all horizontal directions as, for example, in the directions towards and away from the first ends 738, as well as in vertical directions.

The component, including leads 736 is provided on the bottom surface of the support structure. Here again, the component may be fabricated in place on the bottom surface. The support structure holds the second ends of the leads in position, and prevents the leads from flexing. The support structure is then engaged with a wafer or other microelectronic device 748 and the second ends of the leads 740 are bonded to the contacts 750 using bonding material carried on the second ends or on the contacts. As described in copending, commonly assigned U.S. patent application Ser. No. 09/233,586, filed Jan. 19, 1999, the disclosure of which is hereby incorporated by reference herein, the leads used in this embodiment, and in the other embodiments discussed above, may be provided with surfaces which are not wettable by the liquefied bonding materials bounding the second ends of the leads, so that the liquefied bonding material does not tend to spread along the leads towards the first ends thereof during the bonding process. After the second ends of the leads have been bonded to the contacts, the connecting layer 734 is degraded as, for example, by application of radiant energy or heat. The structural layer of support structure 730 is removed. A compliant encapsulant (not shown) may be deposited over and around the leads, leaving the first ends or terminals 738 exposed. The leads, once freed from the support structure, allow movement of the contacts on the chip relative to the first ends or terminals 738. In methods according to this aspect of the invention, the support structure stabilizes the lead second ends and allows accurate alignment of the lead second ends with the contacts on the wafer or microelectronic element. Stated another way, in this process the leads are bonded to the microelectronic component while a first condition in which leads are constrained, and then the leads are brought to a second condition in which the leads are unconstrained, by releasing the lead tip ends from the support and, preferably, by removing the support.

In a variant of this approach, support 730 can include a sacrificial layer and the process of freeing the leads from the support may include degrading the connecting layer so as to free the sacrificial layer and then etching the sacrificial layer. According to a further variant, the structural layer of the support may be an aluminum or other metal susceptible to etching. This approach however is less preferred inasmuch as it may expose the wafer to the etchant. In a further variant of this approach, dielectric layer 735 may incorporate a compliant layer to facilitate movement of the terminals 738 relative to the microelectronic device in the finished assembly.

Figure 24:
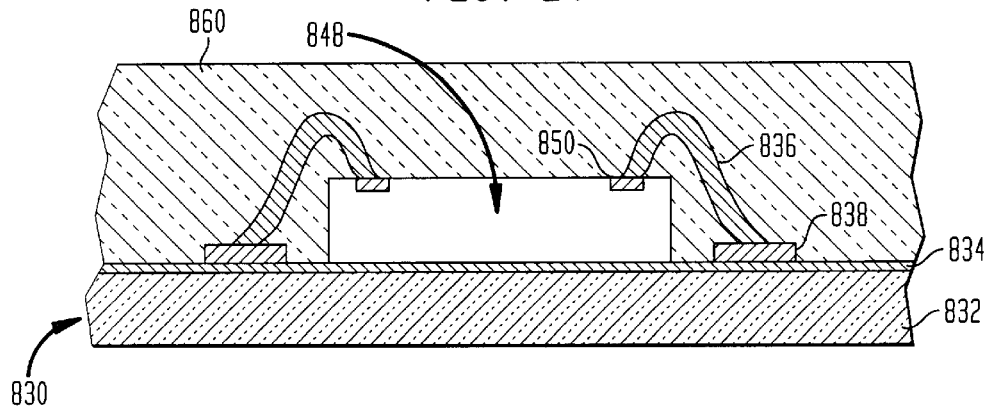
FIG. 24 is a sectional view of components according to a further embodiment of the invention.

In a process according to a further variant of the invention, the electrically conductive elements held on the support structure 830 (FIG. 24) include terminals 838 disposed on a connecting layer 834. A microelectronic element in the form of a chip 848 is disposed on the support structure along with the electrically conductive terminals 838. The chip is disposed in a "face up" arrangement so that the contacts 850 on the chip face away from the support structure. Wire bonds 836 are connected between contacts 850 and terminals 838. Following wire bonding, a dielectric layer 860 is cast over the structure and then connecting layer 834 is degraded so that the structural layer 832 of the support structure can be removed. This leaves a complete, encapsulated chip assembly including the dielectric mass with the chip and wire bond embedded therein, and with the contacts 838 exposed at the bottom surface. The chip is also exposed at the bottom surface so as to promote heat conduction from the chip. The finished assembly is generally similar to certain assemblies disclosed in International Patent Publication WO 97/39482, the disclosure of which is hereby incorporated by reference herein. Other assemblies as shown in the '482 patent publication may also be fabricated using similar techniques. However, in the preferred assembly fabrication techniques according to this aspect of the present invention, it is not necessary to remove a sacrificial layer by processes such as etching or laser ablation.

Figure 25:
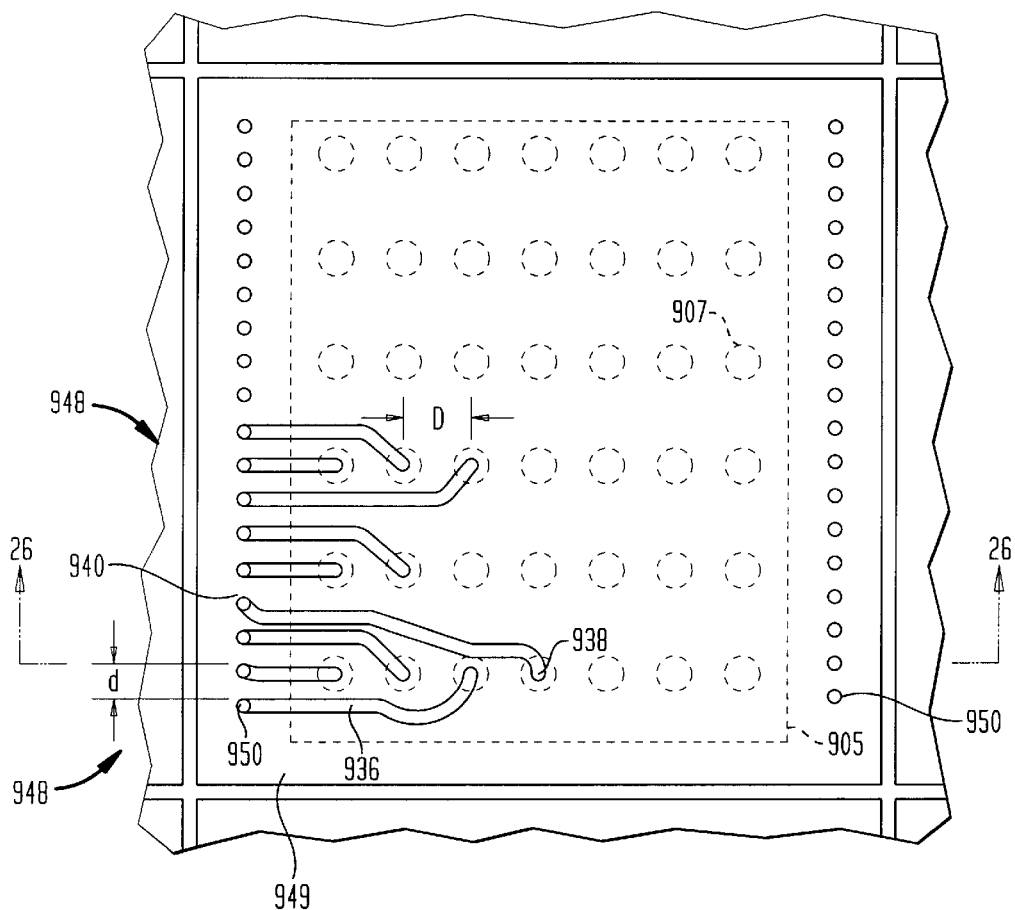
FIG. 25 is a fragmentary top plan view of a wafer in accordance with a further embodiment of the invention.

A wafer 948 partially depicted in FIG. 25 includes a large number of semiconductor chips 949. Each chip has a large number of contacts 950 disposed in one or more rows of adjacent contacts. The contacts within each row lie at a relatively small center-to-center distances d, typically less than about 100 microns. Leads 936 are formed on the top surface of the wafer. Only a few of the leads are depicted in FIG. 25. In practice, there may be tens or hundreds of contacts and a corresponding number of leads. Each lead 936 has contact end 940 connected to a contact 950 on the chip and has a tip end 938 releasably secured to the top surface of the chip or wafer. For example, the chips on the wafer may have a polyimide coating 901 overlying their top surface 903, and the tip ends of the lead may be peelably connected to this polyimide coating. The leads 936 typically are about 15–75 micrometers wide and more typically about 25–50 micrometers. This width dimension is comparable to the diameter of an individual contact 950.

The tip ends 938 of the leads are disposed in a "area array", i.e., an array of regularly spaced tip ends 938 in a two dimensional grid pattern. This grid pattern is disposed in a central area 905 of the chip top surface, inside of the area bounded by the rows of contacts 950. That is, the leads 936 "fan-in" or extend inwardly, toward the center of the chip front surface, from contacts 950 to tip ends 938. As best appreciated with reference to FIG. 25, the spacings D between adjacent lead tip ends 938 are larger than the spacings d between adjacent contacts and contact ends 940 of the leads.

The wafer 948 may be engaged with a further element having pads 907 on a bottom surface. In the particular embodiment depicted in FIG. 26, the further element includes a support 930 including a structural layer 932 and connecting layer 934 as described above, having a set of individual tiles 935 held on the structural layer by the connecting layer 934. The pads 907 are defined by metallic conductive elements on the tiles. For example, pad 907a is defined by a metallic via extending entirely through the tile to a terminal 909 exposed at the top surface of the tile. Other pads such as pad 907b are defined by metallic structures connected to internal conductive elements such as traces within the tile.

Pads 907A are considerably larger in diameter than the contacts. Typically, the pads are about 150 to about 400 microns in diameter, and more preferably about 250 to about 300 microns in diameter. These pads typically are about the same diameter as the terminals 909 exposed at the top surface. These terminals in turn typically are sized to hold solder balls. Pads 907 are disposed in an area array corresponding to the array of lead tip ends 938. The layout of pads 907 is shown in broken lines, superposed on the leads. As will be appreciated from FIG. 25, the larger center-to-center distance between pads 907 allows for the greater diameter of the pads.

The support 930, with the tiles 935 and pads 907 is aligned with the wafer and engaged therewith in the manner discussed above. Either the pads 907 or the lead tip ends 938 carry bonding material (not shown). The bonding material is activated to secure the lead tip ends to the pads. After bonding, the support may be moved away from the wafer to peel a portion of each lead adjacent the tip end 938 away from the wafer and thereby provide a more flexible interconnection between the tiles and the wafer. In the same manner as discussed above, a liquid material adapted to form a dielectric layer may be injected between the support and the wafer and cured, whereupon the structural layer 932 of the support is removed by degrading connecting layer 934.

Figure 26:
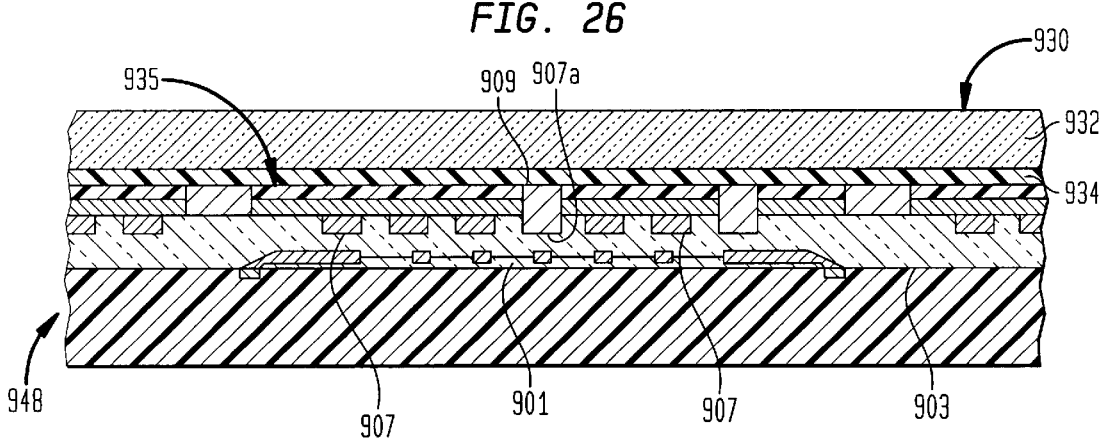
FIG. 26 is a fragmentary sectional view along line 26—26 in FIG. 25, depicting the wafer in conjunction with a further element.
Figure 27:
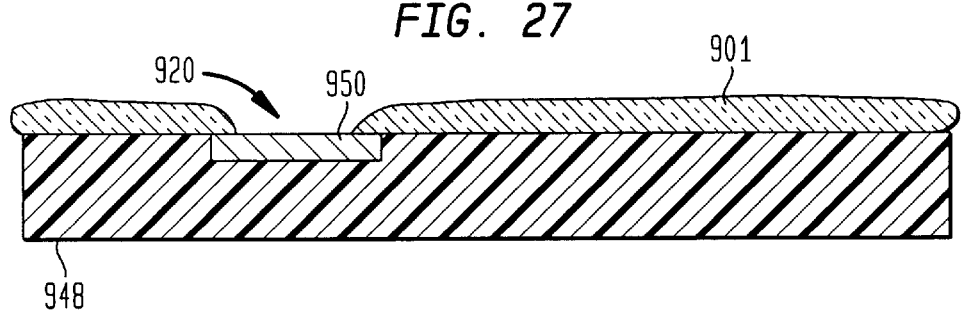
FIGS. 27–30 are fragmentary sectional views depicting portions of a wafer during a lead-forming process.
Figure 28:
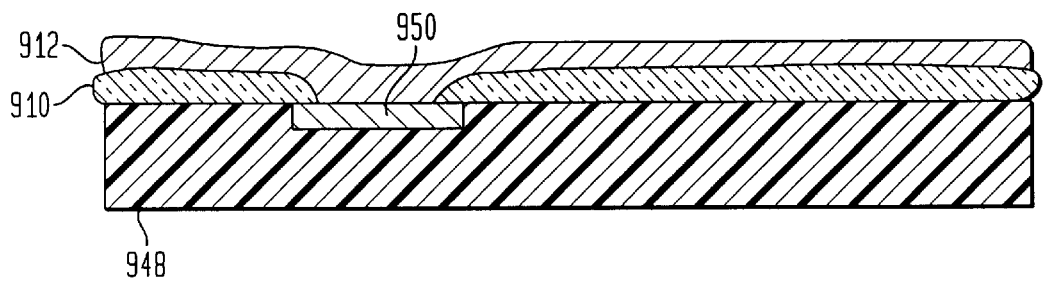
Figure 29:
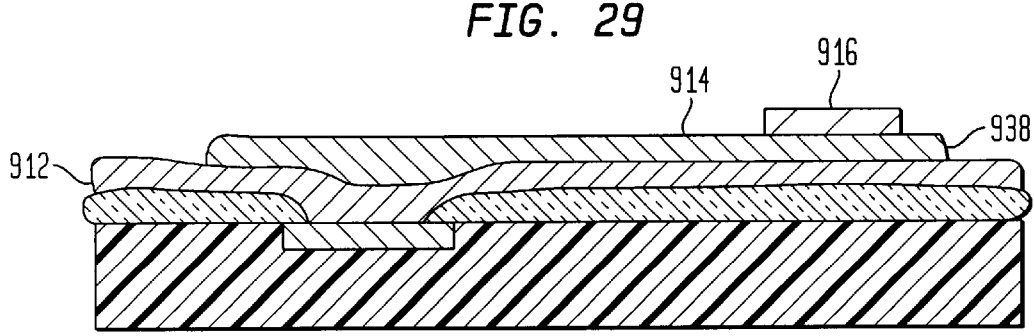
Figure 30:
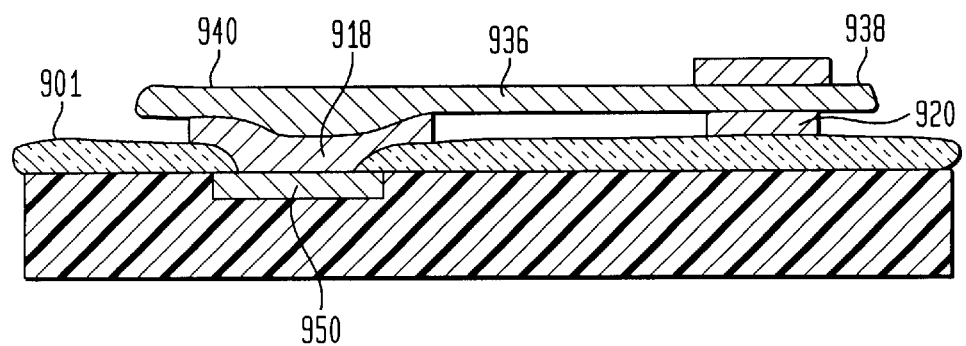

In the embodiment of FIGS. 25 and 26, the leads are formed in place on the top surface of the wafer. Therefore, the contact ends of the leads can be aligned precisely with the contacts 950 of each chip; such alignment can be as precise as the photographic patterning equipment used to fabricate the wafer. The tip ends 938 must be aligned with the pads 907 during the bonding process by an operation involving alignment of support structure 930 with the wafer. However, because the pads have substantially greater diameters than the contacts, the alignment tolerance in this operation is substantially increased by performing the bonding between the tip ends of the leads and the pads 907, rather than between the contact ends of the leads and the contacts. This relatively large tolerance is also enhanced by the fact that the leads have widths substantially smaller than the diameters of pads 907, and hence substantially smaller than the widths of the pads in directions transverse to the contact ends of the leads. All that is necessary to form the correct bond is that the lead tip end engage the pad 907 at any point on the pad surface, so that the lead tip end can bond with the pad 907. A method of forming peelable leads on a surface of a wafer is illustrated diagrammatically in FIGS. 27–30. A wafer 948 having contacts 950 thereon is provided with the polyimide layer 901. The polyimide layer is thick enough to provide a continuous, pinhole-free 3–15 μm. The polyimide layer is spun on using conventional "coater-developer" techniques. In these techniques, an uncured polyimide resin is coated onto the surface by applying the resin and spinning the wafer to distribute the resin. Apertures 920 are formed at each contact 950 by conventional techniques during or after curing. A relatively thick aluminum layer 912 (FIG. 28), such as a layer about 0.5 to 1 μm thick, is deposited over the polyimide layer and over the contacts. Next, a metal such as copper or gold is selectively deposited on the aluminum layer 912 as by electroplating using masks (not shown) to provide openings in the areas where the leads are desired. Using similar masking techniques, a bonding material such as tin, solder or other electrically conductive bonding material 916 is deposited onto the regions which will form the tip ends 938 of the leads. Finally, after removing the masking layers, the wafer is exposed to an etchant which attacks aluminum but which does not substantially attack the metal of the leads. The etchant removes the aluminum in the regions not covered by the leads. However, a first connector 918 is left at the contact end 940 of each lead, permanently connecting such end to the associated contact 950. A small button of aluminum 920 is left at the tip end 938 of each lead, thereby releasably securing the tip end of the lead to the polyimide layer 901. Depending upon the configuration of the leads, connectors 918 and buttons 920 may be formed without further masking. Thus, where the ends 940 and 938 are wider than the other portions of the leads, the aluminum will be removed from beneath the other portions of the leads while some aluminum remains beneath the ends. Alternatively, where the leads are of uniform width, a masking material may be photographically patterned on the ends of the leads and left in place during all or a portion of the etching procedure.

A further process for forming leads on a wafer or chip is depicted in FIGS. 31A–31J. The process begins with a wafer 1148 having a passivation layer 1149 such as an oxide or nitride layer or a polymeric layer on a top surface and having contacts 1150 exposed through apertures in the passivation layer. A photoimageable dielectric material such as a photoimageable resist of the type commonly used in semiconductor processing operations is applied, imaged and developed so as to form a dielectric layer 1152 with apertures aligned with the contacts 1150. A thin tie coat 1154 of nickel or other adhesion-promoting material is sputtered onto the dielectric layer and contacts, whereupon a further photoimageable resist 1156 is applied, imaged and developed so as to form openings 1157 in the regions where leads are to be deposited. Each opening has an end aligned with a contact 1150 and an end remote from the contacts.

Figure 31A:
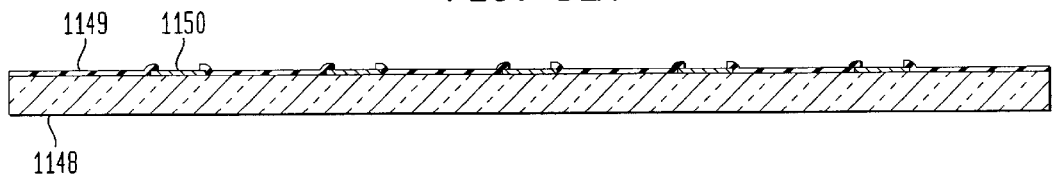
FIGS. 31A–31J are fragmentary sectional view depicting portions of a wafer during a further lead-forming process.
Figure 31B:
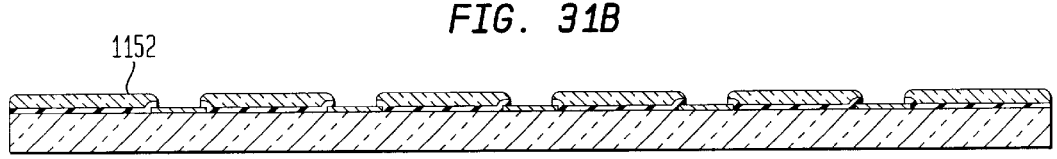
Figure 31C:
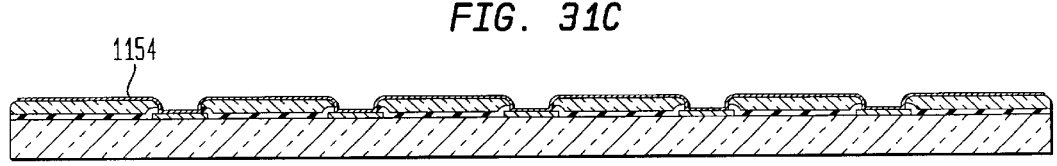
Figure 31D:
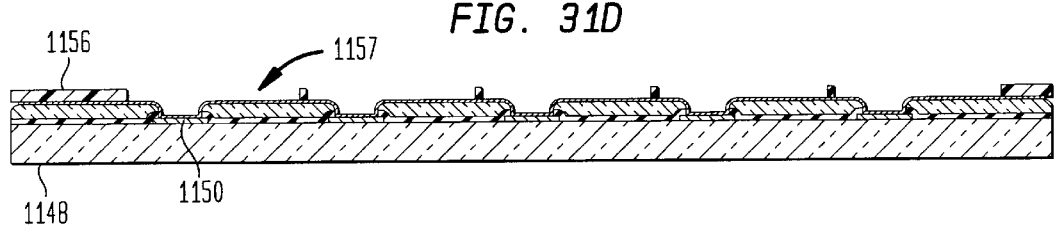
Figure 31E:
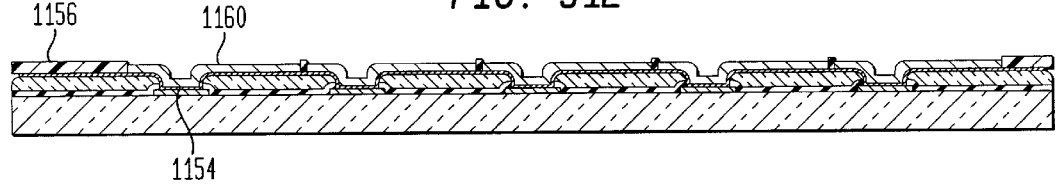
Figure 31F:
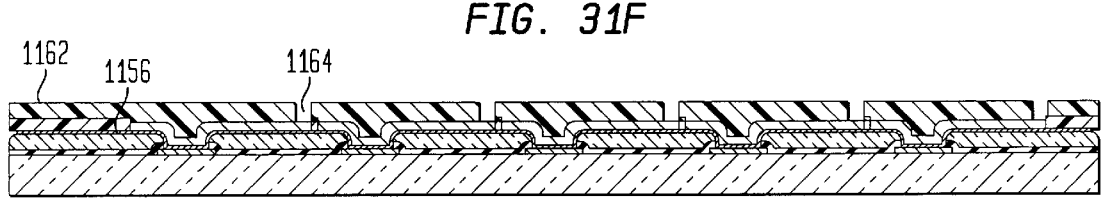
Figure 31G:
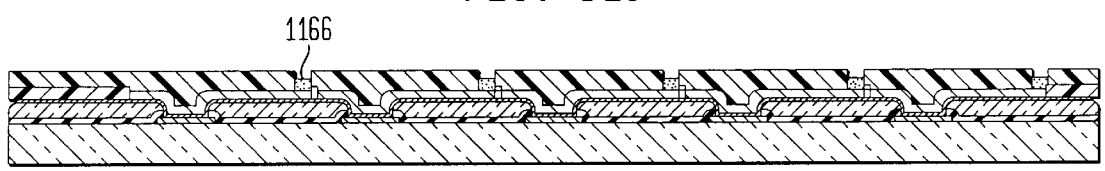
Figure 31H:
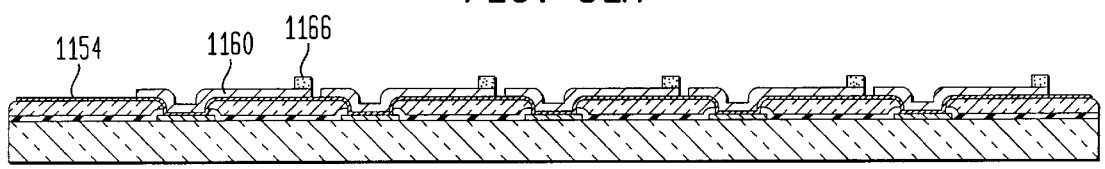
Figure 31I:
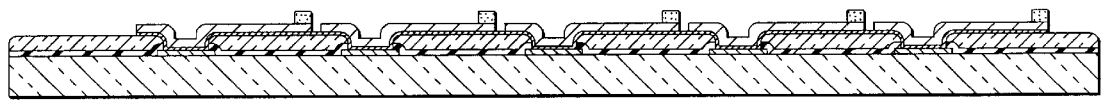
Figure 31J:
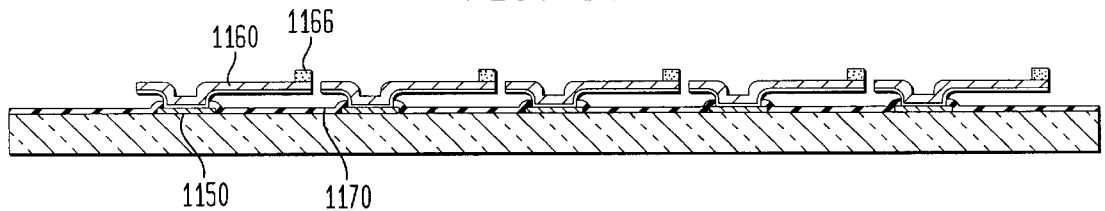

A lead-forming metal such as copper, gold or alloys or combinations thereof is then plated onto the exposed surface of the tie coat 1154 in openings 1157 so as to form leads 1160. A further resist 1162 is applied over resist 1156, imaged and developed so as to leave apertures 1164 at the ends of the leads remote from contacts 1150. Masses 1166 of a bonding material are deposited in these apertures. Resists 1162 and 1156 are then stripped away by conventional processes (FIG. 31H), leaving the tie coat 1154 exposed except in those areas covered by the leads. The tie coat is etched by a brief etching process, commonly referred to as microetching, which does not substantially affect the leads or bonding material, as depicted in FIG. 31I. The first-deposited dielectric layer or resist 1152 is then removed, as depicted in FIG. 31J. The process leaves leads 1160 with first ends attached to the contacts 1150 of the wafer and with second or tip ends 1170 remote from the contacts overlying the wafer surface but detached therefrom.

Figure 32:
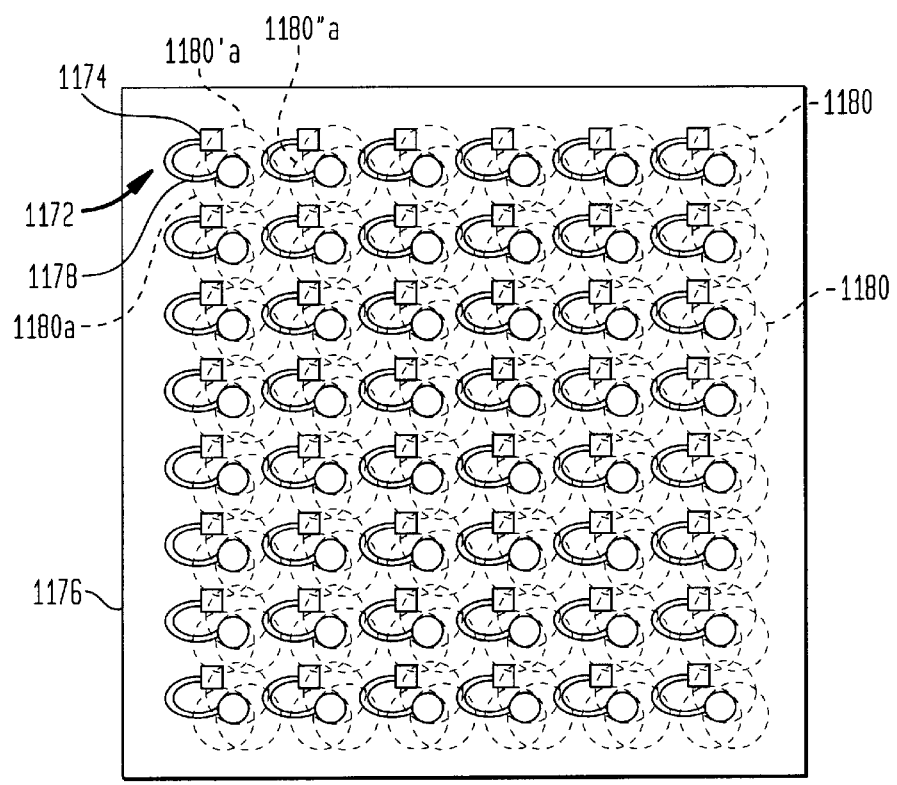
FIG. 32 is a diagrammatic view of a chip and a set of contacts.

A wafer having leads 1160 thereon may be used in processes as discussed above, such as the process discussed above with reference to FIGS. 25–26. Here again, the lead tip ends 1170 can be engaged and bonded to contacts on another element such as a connection Desirably, the leads are deformed by moving the wafer and connection component away from one another. As explained above, formation of the leads on the wafer provides significant advantages in that the leads can be precisely located on the wafer. Moreover, the tip ends can be engaged with contacts which may be larger than the contacts on the wafer, which substantially eases the requirements for precise alignment between the tip ends and the contacts. This effect is illustrated in FIG. 32. The leads 1172 have fixed ends 1174 attached to contacts on a chip 1176. The tip ends 1178 of the leads are engaged with contacts 1180 on a second element such as a connection component, the contacts being shown in broken lines. The contacts may move over a range of positions which is large relative to the tip ends of the leads and still make satisfactory connections to the tip ends. For example, the contact at position 1180a may be in position 1180a' or 1180a", or any position intermediate between positions these positions and still make a satisfactory connection to lead tip end 1178.

In a variant of the process discussed above with reference to FIGS. 31A–31H, the process used to remove the dielectric layer 1152 from beneath leads 1154 is a controllable process such as plasma etching, and the process is controlled as discussed above with reference to FIG. 11 to leave polymeric connecting elements at the tip ends of the leads, holding the leads in position until the tip ends have been bonded to another element. In a further variant of this process, the polymeric layer 1152 is omitted, and the tie coat 1154 is deposited directly over the passivation layer of the chip. The lead tip ends are detached from the chip by etching the passivation layer away after removing the other resists. Processes discussed above with reference to forming leads on wafers may also be applied to form leads on individual semiconductor chips. Processes for forming leads on semiconductor elements may use the techniques disclosed in commonly assigned U.S. Provisional patent application Ser. No. 60/106,055, filed Oct. 28, 1998, the disclosure of which is hereby incorporated by reference herein.

Figure 33A:
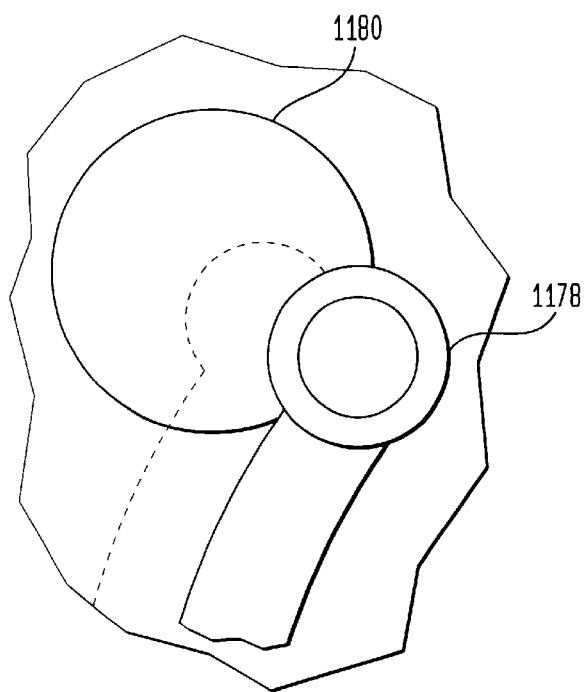
FIGS. 33A and 33B are fragmentary, diagrammatic sectional views depicting portions of leads and contacts during joining processes.

As described in greater detail in the commonly assigned United States Provisional Patent Application entitled "Detachable Lead Structures and Methods" filed of even date herewith and naming David Light and John Smith as inventors (hereinafter, the "Light et al. Application"), the disclosure of which is hereby incorporated by reference herein, the tip ends of leads may be centered on the mating pads by surface tension in a liquid bonding material. As schematically shown in FIG. 33A, the lead may initially be placed in a partially misaligned condition, depicted in solid lines, such that there is only a small region of overlap between the tip end 1178 of the lead and the pad 1180. The lead tip end bears a bonding material such as a solder or eutectic bonding alloy 1182 adapted to form a liquid phase during the bonding operation, and adapted to wet the surface of pad 1180. A portion of the liquefied bonding material 1182 is disposed between the tip end of the lead and the pad, and wets both of these elements. The remainder of the bonding material is not disposed between the tip end and the pad. Therefore, surface tension tends to pull the liquefied bonding material into the relatively small space between the tip end and the pad. This action also moves the tip end of the lead, ultimately bringing the tip end of the lead to a fully aligned condition depicted in broken lines in FIG. 3 at 1180'. Even in an embodiment where a liquefied bonding material is not used, large pads, where the lead has a relatively large degree of overlap with the pad, make electrical connections with the lead tip ends over a wide range of tip end positions.

Figure 33B:
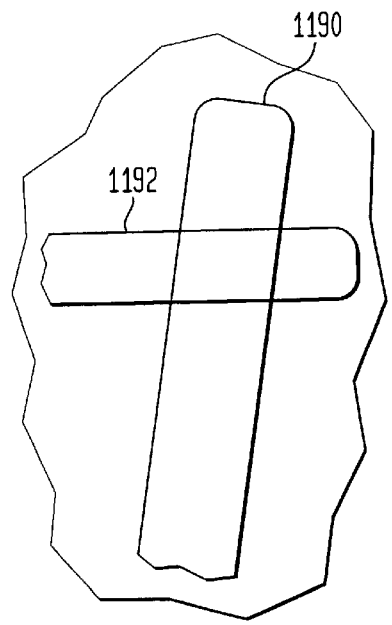
Figure 33C:
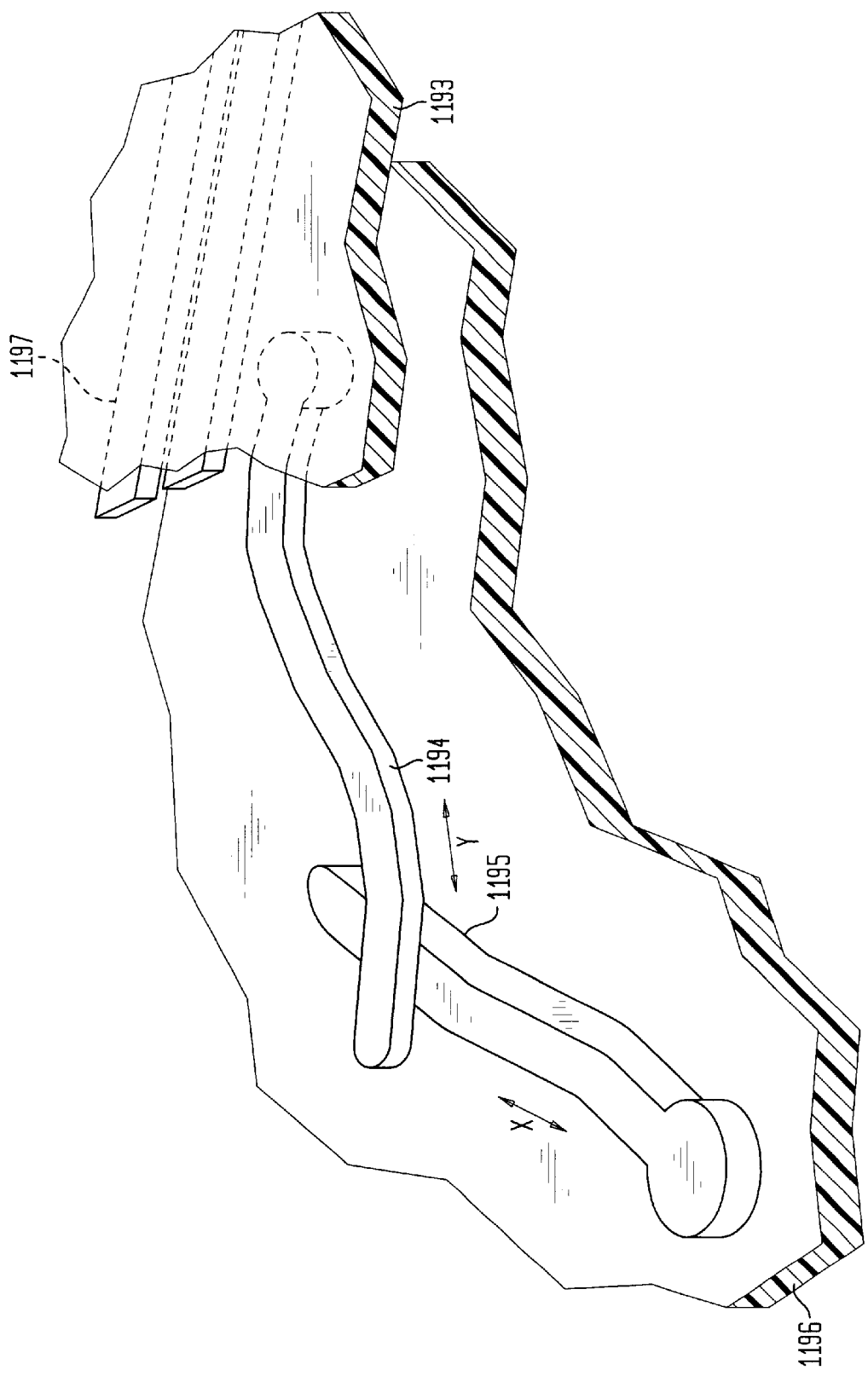
FIG. 33C is a diagrammatic perspective view depicting portions of leads during a further joining process.

As shown in FIG. 33B, the pads 1192 engaged with the tip ends of leads 1190 may be elongated elements having directions of elongation transverse to the direction of elongation of the lead 1190 at the tip end of the lead. This arrangement conserves space within the pad-bearing element and on the pad-bearing surface, but still provides good tolerance for misalignment between the lead tip and the pad. Provided that the nominal position of the lead tip is selected so that the lead tip projects slightly beyond the pad, misalignment in the direction along the lead simply shifts the pad relative to the lead. Misalignment in the transverse direction shifts the lead along the long direction of the pad. The measures discussed with reference to FIGS. 33A and 33B can be applied regardless of whether the pads are on a semiconductor device such as a wafer or on a connection component or other element.

In a process according to a further variant, the pads on the bottom surface of an element 1193 are provided in the form of lead sections 1194 which extend transversely to the tip regions of leads 1195 on chip or wafer 1196. At the inception of the process, the lead sections 1194 lie flat against the bottom surface of element 1193, whereas the leads 1195 lie flat on the top surface of chip 1196. The tip ends of the leads 1195 are bonded to lead sections 1194 so as to form composite, generally L-shaped leads extending between the elements. After the bonding operation, element 1193 and the chip or wafer 1196 are moved away from one another. During such movement, the composite, L-shaped leads are deformed to a vertically-extensive disposition, by bending leads 1195 away from the chip and by bending lead sections 1194 away from element 1193. Stated another way, in this embodiment the pads on the bottom surface of element 1193 are themselves elongated leads. This arrangement provides substantial tolerance for misalignment. misalignment in the X direction (the direction of elongation of leads 1195) will simply shift the region where bonding occurs along leads 1195, whereas misalignment in the Y-direction parallel to lead portions 1194 will simply shift the bonding region along the lengths of lead portions or pads 1194. Moreover, lead portions 1194 of substantial length can be accommodated on the bottom surface of element 1193 while still leaving substantial space for routing Y-direction traces 1197 extending parallel to lead portions 1194 on the bottom surface. X-direction traces (not shown) can be placed on the top surface of element 1193 or within such element. The use of composite, generally L-shaped leads is discussed in greater detail in copending, commonly assigned U.S. patent application Ser. No. 09/281,688 filed Mar. 18, 1999 the disclosure of which is hereby incorporated by reference herein.

A wafer 1048 (FIG. 34) includes a set of chips 1049, each having contacts 1050 disposed in a pair of rows adjacent the center of the chip top surface. Leads 1036 include trace portions 1002 extending outwardly from the contacts, and curved portions 1004 at the outer ends of the trace portions defining the tip ends 1038 of the leads. In this arrangement, the leads "fan-out" from the contacts 1050. Curved portions 1004 of the leads are releasably connected to the chip top surface. For example, the leads may be fabricated as discussed above. Alternatively, the chip may bear a layer of polyimide or other dielectric and the dielectric may be etched from beneath the leads in a manner similar to the etching of polyimide discussed above with reference to FIGS. 11–12.

Figure 34:
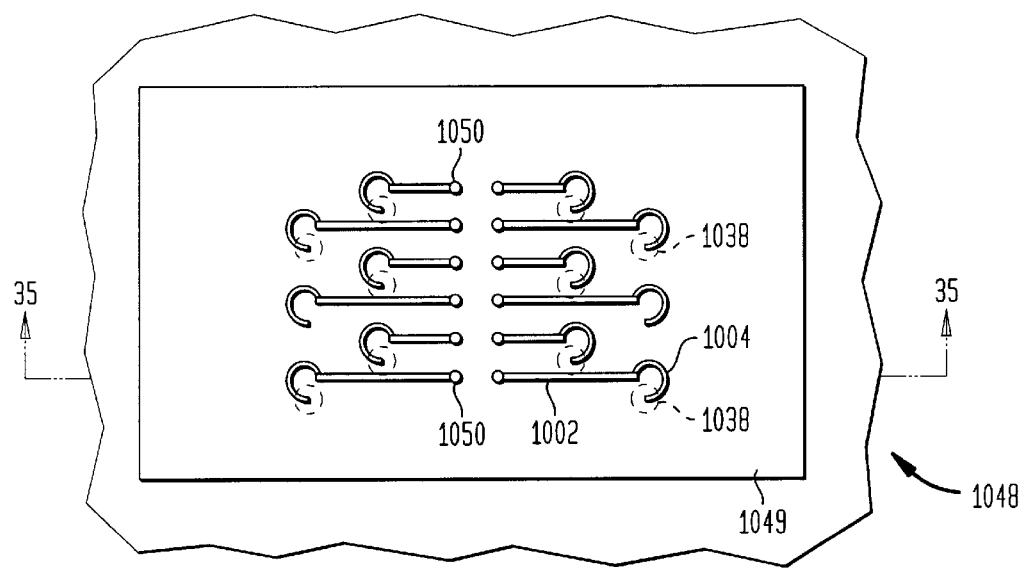
FIG. 34 is a fragmentary top plan view depicting a wafer in accordance with yet another embodiment of the invention.
Figure 35:
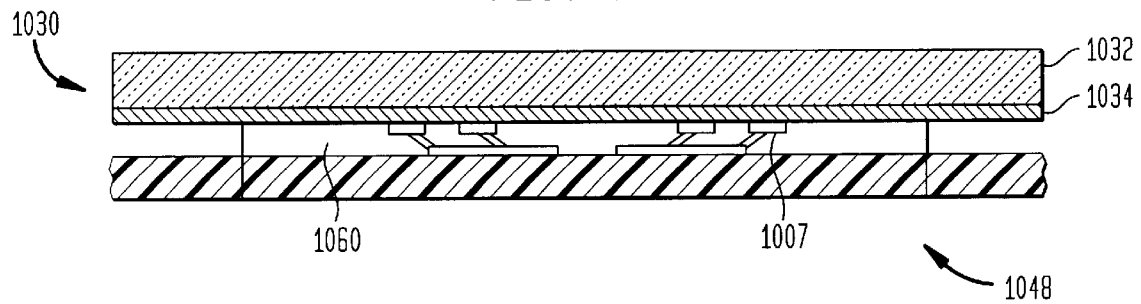
FIG. 35 is a sectional view taken along line 35—35 in FIG. 34, showing the wafer in conjunction with a further element during a process.
Figure 36A:
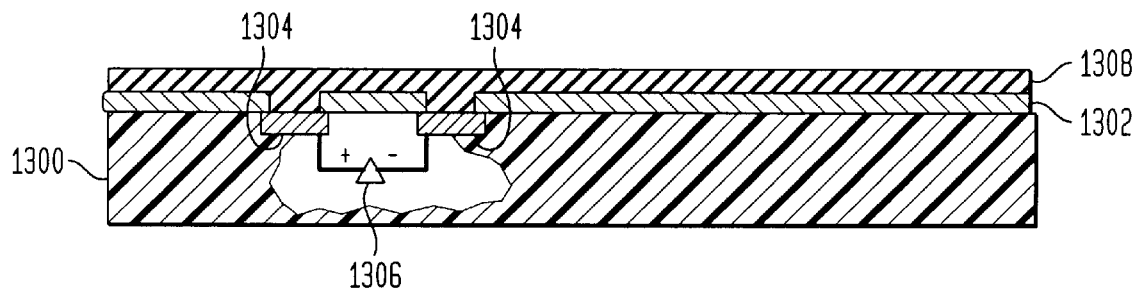
FIGS. 36A–36D are fragmentary sectional views of a wafer during a lead-forming process in accordance with a further embodiment of the invention.
Figure 36B:
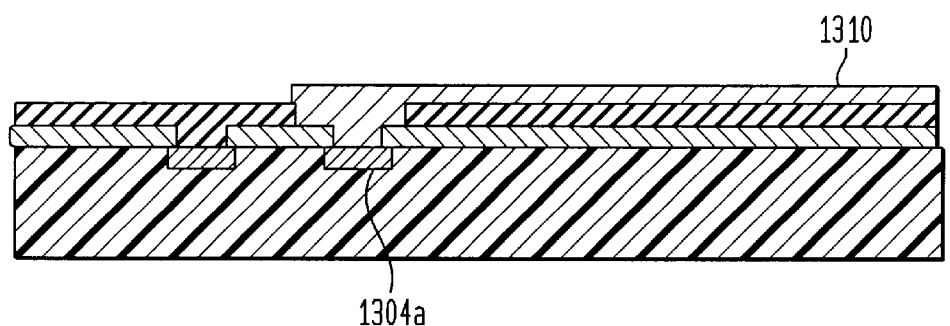
Figure 36C:
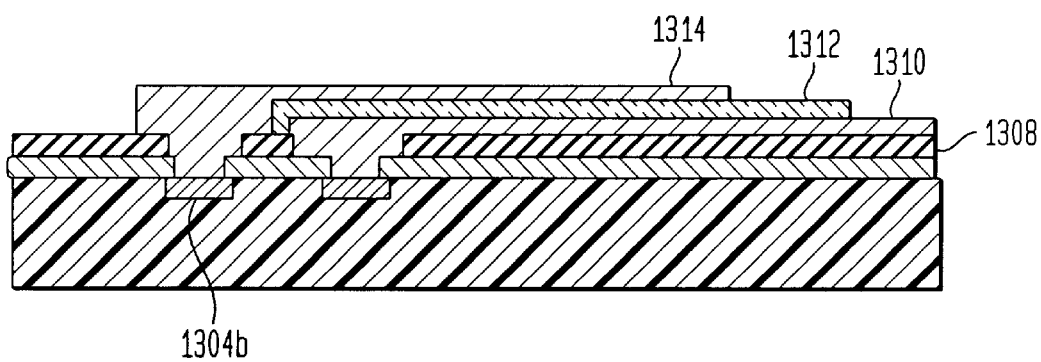
Figure 36D:
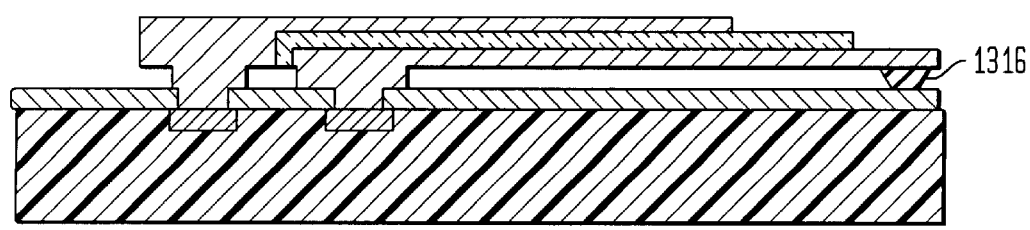

The wafer of FIG. 34 is used in conjunction with a further element including a set of electrically conductive pads 1007 (FIG. 35) carried on a connecting layer 1034, which in turn is carried on the bottom surface of a structural layer 1032 of a support 1030. Here again, the pads 1007 are disposed at greater center-to-center distances than the contacts, and the pads are of larger diameter than the contacts. The pads are held in position relative to one another only by the support 1030. After bonding the pads to the tip ends of the leads, the support is moved away from the wafer so as to bend the curved portions 1004 of the leads, and a dielectric layer 1060 is formed by introducing a curable liquid into the space between the support and the wafer. After degrading the connecting layer 1034, the support is removed, leaving the pads 1007 exposed as terminals on a surface of the dielectric layer 1060.

Numerous variations and combinations of the features discussed above may be utilized. For example, in the embodiments discussed above, a chip or wafer is connected to pre-formed conductive structures such as conductive structures on a connection component. However, as discussed in greater detail in commonly assigned International Publication WO 98/28955, the disclosure of which is hereby incorporated by reference herein, leads connected to a component such as a chip, wafer or other microelectronic element can be connected to a sheet of conductive material. The sheet may be moved away from the component to bend the leads, and a flowable material may be injected between the sheet and component to form a dielectric layer. The sheet may then be etched selectively to leave portions of the sheet as terminals connected to the leads. In a further variant, leads connected to a microelectronic element may be attached directly to a circuit panel such as a circuit board, rather than to a connection component.

Multiconductor leads may be formed on a chip or wafer. For example, as shown in FIGS. 36A–36D, a wafer 1300 having a passivation layer 1302 has contacts 1304 aligned with openings in the passivation layer. The contacts are arranged in sets, with the contacts of each such set being disposed adjacent to one another. The contacts of each such set may be connected to a single electronic device such as a differential signal transmitter 1306 as discussed above with reference to FIG. 21. A conductive sacrificial layer 1308 is applied over the passivation layer (FIG. 36A) and patterned to form an opening aligned with a first contact 1304a of each set. A lead-forming metal is applied in a pattern so as to form a first conductor 1310 overlying the sacrificial layer connected to the contact 1304a of each set. A dielectric material such as a polyimide is applied and selectively patterned, as by photographically patterning the dielectric or etching the dielectric using a resist (not shown). The dielectric forms dielectric layers 1312 overlying the first conductor 1310 and first contact 1304a of each set, but not covering the second contact 1304b of each set. After selectively etching the sacrificial layer 1308 to form openings aligned with the second contact 1304b of each set, a further layer of lead-forming metal is applied and patterned so as to form second conductors 1314 overlying the first conductors but insulated therefrom by the dielectric layers 1312, each such second conductor being connected to the second contact 1304b of a set. The wafer is then treated with an etchant which attacks the sacrificial layer so as to remove the sacrificial layer. As discussed above, the etching process and feature design may be controlled so as to leave small anchors 1316 at the tip end of each lead. The wafers according to this aspect of the invention can be used with mating elements having contacts arranged in sets. Thus, the conductors 1314 and 1310 of each lead can be bonded to contacts disposed adjacent one another on a connection component, and the connection component and wafer may be moved away from one another. A flowable material may be injected to form a compliant dielectric layer as discussed above, and the wafer and connection component may be severed to form packaged chips. Alternatively, the wafer with the multilayer leads thereon may be severed to form individual chips having such leads. The individual chips may be assembled to connection components to form packaged chips or, alternatively, may be assembled to circuit panels such as circuit boards. In this case, the chip optionally may be moved away from the circuit board, so as to deform the leads, and a flowable material may be injected around the leads. The same processes may be used to make and process chips or wafers with multiconductor leads having more than two conductors per lead.

Figure 37:
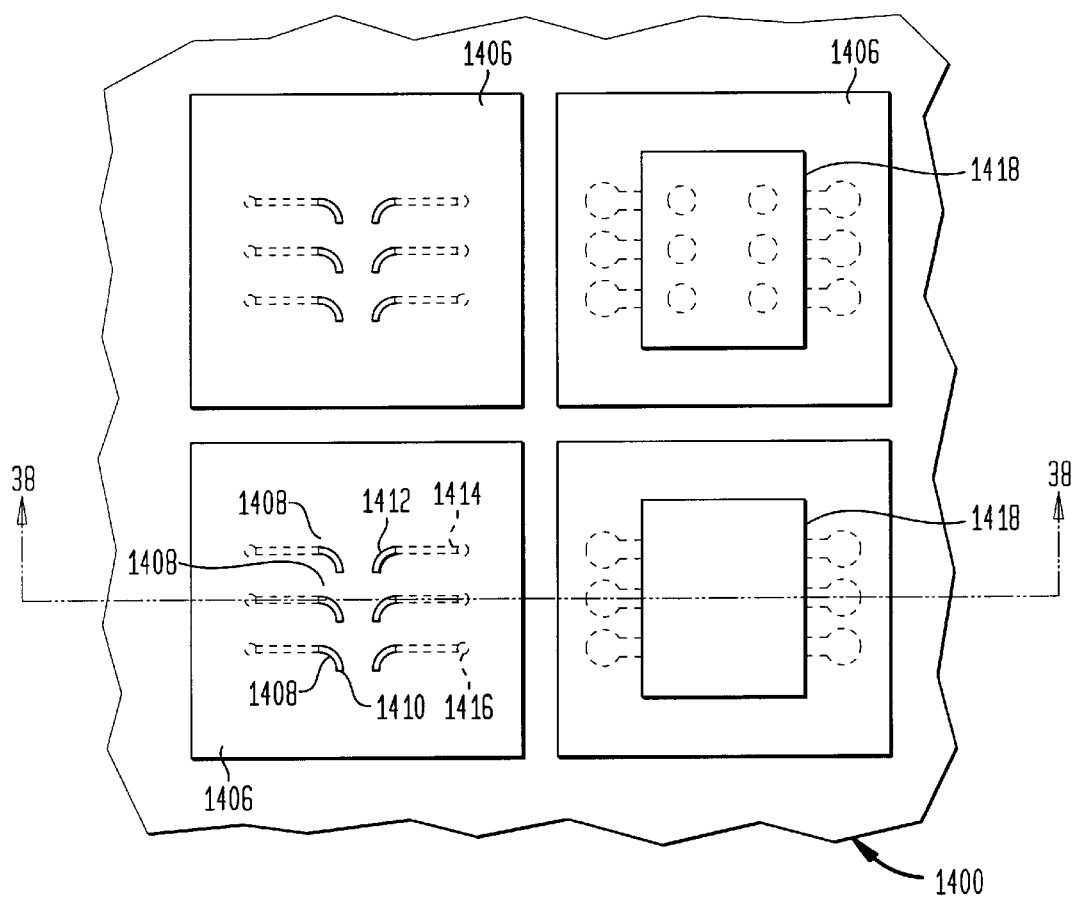
FIG. 37 is a fragmentary view depicting a component in accordance with a further embodiment of the invention, in conjunction with semiconductor chips.
Figure 38:
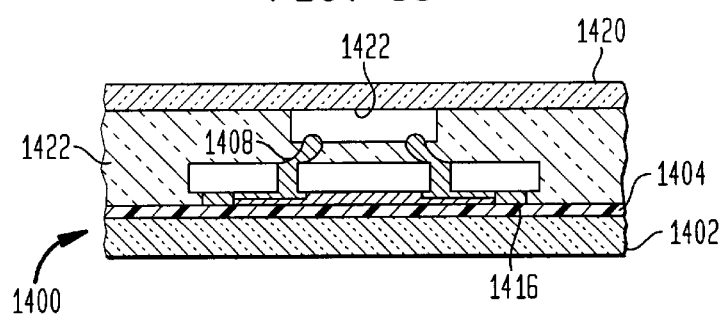
FIG. 38 is a sectional view taken along line 38—38 in FIG. 37 but depicting the component and chip at a later stage of processing.

A component according to a further embodiment of the invention (FIGS. 37–38) includes a support structure 1400 including a transparent structural layer 1402 and connecting layer 1404 susceptible to degradation by radiant energy. A set of tiles 1406 generally similar to those discussed above with reference to FIGS. 13–17 is provided on connecting layer. However, each tile has conductive features arranged in a "fan-out" pattern. Thus, the tiles have leads 1408 with tip or releasable ends 1410 disposed on the side of the tile facing away from the support structure 1400. The releasable ends of the leads are disposed in a central area of the tile. The fixed end 1412 of each lead is connected to a conductive trace 1414 which extends outwardly towards the periphery of the tile to a contact 1416.

In use, individual semiconductor chips 1418 are aligned with the tiles and the contacts of the chips are bonded to the tip ends of the leads. This alignment and bonding step may be performed, for example, by grasping each chip in a chuck attached to a robot and advancing the individual chip onto the tile while applying heat and pressure through the chuck. During this process, the robot may register the position of the chip with the tiles by detecting fiducial marks on the support structure or tiles. Alternatively, a set of multiple chips disposed on a further support at spacings corresponding to the spacings between tiles may be aligned and bonded in a single operation.

After the chips have been bonded to the tiles, the chips and the tiles are moved away from one another by moving the chips away from the support structure 1400. For example, a unitary aluminum or other thermally conductive heat spreader 1420 may be bonded to the rear surfaces 1422 of all of the chips, and the heat spreader may be moved away from the support structure so as to bend leads 1408 to the vertically-extensive condition illustrated in FIG. 38. A flowable material may be injected between the heat spreader and tiles and then cured as discussed above to form a dielectric layer such as a compliant layer surrounding the leads. Desirably, the flowable material is introduced under pressure so that the flowable material provides at least some of the force necessary to cause such movement. The connecting layer 1404 then may be degraded so as to release the tiles from the structural layer 1402, and the heat spreader may be severed to form individual units, each including a tile, a chip and a portion of the heat spreader.

In a variant of this procedure, individual heat spreaders mounted on a common support by a degradable connecting layer such as a UV-degradable layer may be used in place of a unitary support. The individual heat spreaders are separated from the common support after the chips are moved. In yet another variant, the rear surfaces of the chips may be bonded directly to a support by a degradable connecting layer before moving the chips, and then freed from the support. The same process may be applied using chips bearing leads as discussed above, in conjunction with tiles having traces thereon to form the fan-out pattern. In further variants, the pattern of conductive elements on the tiles forms a "fan-in/fan-out" pattern, wherein some of the external connecting terminals 1416 on the tile are disposed in the central area of the tile covered by the chip, whereas other terminals are disposed in the periphery of the tile, outside of the area covered by the chip.

As further described in the Light et al. Application filed of even date herewith, and in the aforementioned U.S. patent application Ser. No. 09/267,058, connections between leads and a support may be degraded by thermal processes such as by application of heat to degrade a heat-degradable adhesive bond or by heating and/or cooling an assembly having a metallic feature weakly adhering to a polymeric layer. Also, the degradation of the bond between a conductive feature such as a lead tip end may occur during the same process step or steps which forms a bond between the conductive feature and a mating feature on an opposing element.

As these and other variations and combinations of the features discussed above can be utilized without departing from the present invention as defined by the claims, the foregoing description of the preferred embodiments should be taken by way of illustration rather than by way of limitation of the claimed invention.

What is claimed is:

1. A method of making a microelectronic assembly comprising:
   (a) providing leads physically connected to a bottom surface of a support, each said lead having a tip end and a terminal end;
   (b) engaging said support with a microelectronic element having contacts thereon so that the tip ends of the leads are aligned with the contacts of the microelectronic element, and bonding the tip ends of the leads to the contacts;
   (c) during or after said bonding, selectively degrading the connection between the support and the leads at and adjacent the tip ends thereof so as to free the tip ends from the support and leave the terminal ends secured to the support.

2. The method as claimed in claim 1 further comprising moving said support through a predetermined displacement away from said microelectronic element after said selectively degrading so as to deform said leads towards a vertically-extensive disposition.

3. The method as claimed in claim 2 further comprising degrading the connection between the terminal ends of said leads and the support after said moving said support away from the microelectronic element.

4. The method as claimed in claim 2 further comprising introducing flowable material around said leads during or after said movement of the support and curing said flowable material to form a dielectric layer surrounding said leads.

5. The method as claimed in claim 1 wherein said microelectronic element includes at least one semiconductor chip.

6. The method as claimed in claim 1 wherein said selectively degrading includes selectively applying radiation through said support at and adjacent to the tip ends of the leads.

7. The method as claimed in 1 wherein providing said leads includes providing said leads with the terminal ends thereof secured to at least one dielectric element mounted on said support, further comprising releasing the at least one dielectric element from the support.

8. The method as claimed in claim 7 wherein said at least one dielectric element includes a plurality of dielectric elements, and wherein said plural dielectric elements are movable with respect to one another upon release of said dielectric elements from said support.

9. A method of making a packaged microelectronic component comprising:
  (a) providing a support including a structural layer and electrically conductive elements secured to said structural layer; then
  (b) connecting said conductive elements to a microelectronic component; and;
  (c) at least partially releasing said conductive features from said structural layer.

10. The method as claimed in claim 9 wherein said structural layer is transparent to radiation in a degradation wavelength band, said features being secured to said structural layer by a connecting layer on a bottom surface of said structural layer, said step of at least partially releasing said features from said structural layer including directing radiation in said degradation wavelength band through said structural layer to degrade said connecting layer.

11. The method as claimed in claim 9 wherein said step of at least partially releasing said features from said structural layer includes changing the temperature of said features.

12. The method as claimed in claim 11 wherein said features are secured to said structural layer by a connecting layer on a bottom surface of said structural layer, said step of at least partially releasing said features from said structural layer including applying heat to degrade said connecting layer.

13. The method as claimed in claim 9 wherein said support carries connection components including dielectric layers, said conductive features include leads having fixed ends secured to said dielectric layers and tip ends projecting from said dielectric layers, said step of at least partially releasing said features from said structural layer being performed so as to at least partially release said tip ends of said leads from said structural layer.

14. The method as claimed in claim 9 wherein said step of connecting said conductive features to a microelectronic component includes providing leads extending between said conductive features and the microelectronic component.

15. The method as claimed in claim 9 wherein said conductive features are carried on a sacrificial layer having etching properties different from the material constituting said conductive features, said sacrificial layer being connected to said structural layer by said connecting layer, whereby degradation of said connecting layer frees said sacrificial layer from said structural layer, the method further comprising etching said sacrificial layer without destroying said conductive elements.

16. The method as claimed in claim 15 wherein said sacrificial layer is electrically conductive, the method further comprising forming said electrically conductive elements in place on said sacrificial layer using plating or etching currents conveyed through said sacrificial layer.

17. The method as claimed in claim 16 further comprising the step of forming one or more dielectric layers in place on said sacrificial layer.

18. The method as claimed in claim 9 wherein said microelectronic component is a semiconductor chip having a front surface with contacts thereon and a back surface, said step of connecting the conductive elements to a microelectronic element including positioning the chip on the connecting layer of the support with the back surface of the chip facing toward the support and the front surface facing away from the support, and connecting leads between the contacts on the chip and the conductive elements while the chip is in place on the support.

19. A method as claimed in claim 18 further comprising applying an encapsulant over the chip and leads and curing the encapsulant in contact with the connecting layer to form a body having a bottom surface facing toward the support, whereby the body is freed from the support when the connecting layer is degraded and the conductive features form terminals exposed to the bottom surface of the body.

20. A mandrel for forming microelectronic elements comprising:
  (a) a structural layer transparent to radiation in a degradation wavelength band;
  (b) an electrically conductive sacrificial layer thinner than said structural layer; and
  (c) a connecting layer securing said sacrificial layer to said structural layer, said connecting layer being degradable by radiation in said degradation wavelength band.

21. The mandrel as claimed in claim 20 wherein said sacrificial layer is formed from a metal selected from the group consisting of aluminum and aluminum-based alloys, copper and copper-based alloys.

22. A structure for forming microelectronic assemblies including:
  (a) a rigid support having a substantially uniform coefficient of thermal expansion;
  (b) a plurality of electrically conductive elements connected to said support by a connecting material, said support being transparent to radiation in a band of wavelengths effective to degrade said connecting material.

23. The structure as claimed in claim 22 further comprising a sacrificial layer, said sacrificial layer being formed from a material different from said conductive elements and being disposed between said conductive elements and said support.

24. The structure as claimed in claim 23 wherein said sacrificial layer is formed from a metal selected from the group consisting of aluminum and aluminum-based alloys, and wherein said conductive features are formed from a metal selected from the group consisting of copper, gold and alloys thereof.

25. The structure as claimed in claim 23 wherein said sacrificial layer is formed from a metal selected from the group consisting of copper and copper-based alloys, and wherein said terminals are formed from a metal selected from the group consisting of gold and gold-based alloys thereof.

26. An element as claimed in claim 22 wherein said electrically conductive elements include leads.

27. An element as claimed in claim 22 wherein said electrically conductive elements include terminals.

28. An element as claimed in claim 27 further comprising a sheetlike dielectric layer, said terminals being exposed at a top face of said dielectric layer facing toward said support.

29. A method of making a plurality of packaged microelectronic components comprising the steps of:
  (a) providing:
    (i) a temporary support with a plurality of dielectric elements thereon, each said dielectric element having electrically conductive features thereon;
    (ii) a plurality of microelectronic devices, and
    (iii) a plurality of leads, said leads having first ends connected to conductive features on said dielectric elements and having second ends attached to said microelectronic devices; and (b) at least partially removing said temporary support so as to allow said dielectric elements to move relative to one another.

30. The method as claimed in claim 29 further comprising moving said microelectronic devices and said support away from one another so as to bend the second ends of said leads away from said support while leaving the first ends of said leads in position on said support before said at least partially removing said support.

31. The method as claimed in claim 29 wherein providing said temporary support, microelectronic devices and leads is performed by providing said temporary support and dielectric elements with said leads disposed on said dielectric elements and bonding said second ends of said leads to contacts on said microelectronic elements.

32. The method as claimed in claim 31 wherein providing said temporary support with said dielectric elements leads thereon includes fabricating said dielectric elements and said leads on said temporary support.

33. The method as claimed in claim 29 wherein providing said temporary support, microelectronic devices and leads is performed by providing said microelectronic devices with leads disposed on top surfaces of said microelectronic devices facing towards said temporary support, and bonding said first ends of said leads to said conductive features on said dielectric elements.

34. The method as claimed in claim 29 wherein said dielectric elements are releasably attached to said temporary support, removing said temporary support including the releasing said dielectric elements from said temporary support.

35. The method as claimed in claim 34 wherein said dielectric elements are releasably attached to said temporary support by a connecting material, and wherein releasing said dielectric elements from said temporary support includes degrading said connecting material.

36. The method as claimed in claim 35 wherein said temporary support is formed from a material transparent to radiation of a predetermined degradation wavelength, and wherein said degrading said connecting material includes applying radiation in said degradation wavelength band through said temporary support.

37. The method as claimed in claim 29 wherein said removing said temporary support includes etching said temporary support.

38. The method as claimed in claim 37 wherein said temporary support includes a sacrificial metal and wherein said etching includes dissolving said sacrificial metal without substantially etching said conductive features.

39. The method as claimed in claim 38 wherein said temporary support includes a structural layer having a coefficient of thermal expansion between of about $1.5 \times 10^{-6}$/°C. to about $6 \times 10^{-6}$/°C. and a layer of said sacrificial metal disposed between said structural layer and said dielectric elements.

40. The method as claimed in claim 38 further comprising forming said conductive features in place on said temporary support, said forming including applying plating or reverse plating currents to metallic elements through said sacrificial metal.

41. The method as claimed in claim 29 wherein said microelectronic devices are provided as a unitary wafer.

42. The method as claimed in claim 41 wherein said temporary support and said wafer have coefficients of thermal expansion which differ from one another by about $6 \times 10^{-6}$/°C. or less.

43. The method as claimed in claim 41 wherein said wafer is formed from silicon and said temporary support has a coefficient of thermal expansion between of about $1.5 \times 10^{-6}$/°C. and about $6 \times 10^{-6}$/°C.

44. The method as claimed in claim 41 further comprising severing said wafer after said removing said support.

45. The method as claimed in claim 29 wherein at least some of said dielectric elements have at least some conductive features arranged in a fan-out pattern so that such features extend between a central region of each such element and a peripheral region, and said step of providing said microelectronic devices includes mounting at least some of the microelectronic devices to said central regions.

46. A component for making packaged microelectronic elements comprising:
(a) a support having a substantially uniform, isotropic coefficient of thermal expansion;
(b) a plurality of separate dielectric elements releasably attached to said support structure, said dielectric elements having conductive features thereon.

47. The component as claimed in claim 46 wherein said support is formed from a material transparent to radiation of a predetermined degradation wavelength, and wherein said dielectric elements are secured to said support by a connecting material degradable by radiation in said degradation wavelength band.

48. The component as claimed in claim 41 wherein said transparent material has a coefficient of thermal expansion of about $6 \times 10^{-6}$/°C. or less.

49. The component as claimed in claim 46 wherein said support includes a sacrificial metal etchable by an etchant which does not substantially attack said conductive features.

50. A component as claimed in claim 49 wherein said support includes a structural layer of a material having a coefficient of thermal expansion of about $6 \times 10^{-6}$/°C. or less and a layer of a sacrificial metal disposed between said first layer and said dielectric elements, said sacrificial metal layer being thinner than said structural layer.

51. A component as claimed in claim 46 wherein said dielectric elements have top surfaces facing toward said support and bottom surfaces facing away from said support, said dielectric elements having leads, said leads having first ends fixed to the dielectric elements and connected to said conductive features, said leads having second ends releasably attached to said dielectric elements.

52. A method of connecting a plurality of leads to one or more microelectronic elements comprising:
(a) providing said leads physically connected to a support by a connecting material so that said leads are maintained in position on the support at least partially by a connecting material;
(b) juxtaposing the support with the microelectronic element so that the leads are aligned with contacts on the microelectronic element;
(c) bonding the leads to the contacts of the microelectronic element; and then
(d) releasing the connection between the leads and the support after said bonding by degrading the connecting material.

53. The method as claimed in claim 52 wherein degrading said connecting material includes directing radiant energy through the support onto said connecting material.

54. A method as claimed in claim 52 wherein said leads are flexible after they are released from the support.

55. A method of making a microelectronic assembly comprising the steps of:
(a) providing a semiconductor element including one or more semiconductor chips, said semiconductor element having contacts on a front surface;
(b) forming leads in place on said semiconductor element overlying said surface, said leads having contact ends connected to said contacts and having tip ends releasably connected to said semiconductor element; then
(c) juxtaposing said semiconductor element and leads with a further element having pads thereon, said pads having an extent in a direction transverse to the tip ends of the leads larger than the widths of the tip ends of said leads, and bonding said tip ends of said leads to said pads.

56. The method as claimed in claim 55 wherein said pads are round pads at least about 150 μm in diameter and said lead tip ends are about 75 μm wide or less.

57. The method as claimed in claim 55 wherein said pads are elongated in directions transverse to the tip ends of the leads.

58. The method as claimed in claim 57 wherein said pads are elongated lead sections, whereby bonding of said lead tip ends to said pads forms generally L-shaped composite leads extending between said semiconductor element and said further element.

59. The method as claimed in claim 55 further comprising moving said further element through a predetermined displacement away from said microelectronic element so as to deform said leads towards a vertically-extensive disposition.

60. The method as claimed in claim 59 further comprising the step of introducing a flowable material around said leads during or after said moving step and curing said flowable material for form a complaint layer surrounding said leads.

61. The method as claimed in claim 55 wherein said further element includes a sheetlike dielectric element having said pads on a bottom surface facing toward said semiconductor element and having terminals on a top surface facing away from said semiconductor element, at least some of said pads being connected to said terminals.

62. The method as claimed in claim 61 wherein at least some of said pads and said terminals are provided as unitary via structures extending through said sheetlike dielectric element, each said via structure having a bottom end forming one said pad and a top end forming one said terminal.

63. The method as claimed in claim 55 wherein said further element includes terminal structures defining said pads, said terminal structures being disposed on a temporary support and connected to one another only by said temporary support, the method further comprising removing said support from said terminal structures after moving said further element and said semiconductor element away from one another.

64. The method as claimed in claim 55 wherein said semiconductor element includes a masking layer having openings at said contacts, said step of forming said leads on said semiconductor element including forming the leads on said masking layer.

65. The method as claimed in claim 55 wherein said contacts are disposed at first center-to-center distances from one another and said pads are disposed at second center-to-center distances larger than said first center-to-center distances.

66. A method as claimed in claim 65 wherein at least some of said first center-to-center distances are less than about 100 μm and at least some of said second center-to-center distances are more than about 200 μm.

67. The method as claimed in claim 55 wherein said further element includes a rigid support having a uniform coefficient of thermal expansion, said pads being held in a preselected pattern on said rigid support at least until completion of said bonding step.

68. The method as claimed in claim 67 wherein said pads are releasably secured to said support, the method further comprising removing said support from said pads after said bonding step.

69. The method as claimed in claim 68 wherein said pads are secured to said support by a connecting material, said removing said support including degrading said connecting material by directing radiation through said support.

70. The method as claimed in claim 67 wherein the coefficient of thermal expansion of said support is substantially equal to the coefficient of thermal expansion of said semiconductor element.

71. An element for forming microelectronic assemblies including:
(a) a rigid support having a substantially uniform coefficient of thermal expansion;
(b) a plurality of electrically conductive structures defining pads facing away from said support, said conductive structures being releasably connected to said support, said pads being about 150 μm to about 400 μm in diameter.

72. An element as claimed in claim 71 wherein said conductive structures are connected to said support by a connecting material, said support being transparent to radiation in a band of wavelengths effective to degrade said connecting material.

73. An element as claimed in claim 71 wherein said conductive structures are connected to said support by a connecting material susceptible to degradation upon heating.

74. An element as claimed in claim 71 wherein said conductive structures are connected to one another only by said support.

75. A semiconductor element comprising:
(a) a semiconductor body having a surface, contacts and circuits within said body connected to said circuits; and
(b) a plurality of leads overlying said surface, said leads having first ends fixed to said body and having second ends displaceable with respect to said body, at least some of said leads being multiconductor leads, each said multiconductor lead including a plurality of conductors and dielectric material insulating said conductors from one another.

76. A semiconductor element as claimed in claim 75 wherein at least some of said contacts are arranged in sets of mutually-adjacent contacts, said sets of contacts being associated with circuits within said body so that for at least some sets of contacts, a plurality of contacts in the same set are connected to the same circuit and to conductors of the same lead.

77. A semiconductor element as claimed in claim 75 wherein said body is a wafer incorporating a plurality of chips, each such chip including contacts and circuits as aforesaid.

78. A method of making a microelectronic assembly comprising assembling a semiconductor device as claimed in claim 75 with a further element so that the conductors of said multiconductor leads are connected to contacts on said further element and moving said further element and semiconductor device away from one another so as to deform said multiconductor leads to a vertically-extensive disposition.

79. A method as claimed in claim 78 further comprising the steps of injecting a flowable material between said semiconductor device and said further element and curing said flowable material to form a layer surrounding said leads.

80. A method as claimed in claim 78 wherein said further element includes an electrically conductive potential plane and one or more of said conductors are connected to said potential plane.

81. A method as claimed in claim 78 wherein said semiconductor element is a wafer incorporating a plurality of chips, and wherein said further element has a CTE substantially matched to the CTE of said wafer.

\* \* \* \* \*

UNITED STATES PATENT AND TRADEMARK OFFICE
CERTIFICATE OF CORRECTION

PATENT NO.   : 6,361,959 B1
DATED        : March 26, 2002
INVENTOR(S)  : Masud Beroz, Joseph Fjelstad, Belgacem Haba and John W. Smith It is certified that error appears in the above-identified patent and that said Letters Patent is hereby corrected as shown below:

<u>Column 29,</u>
Lines 52-53 and 69-70, "$1.5 \times 10^-{}_6/{}^\circ C$" should read -- $1.5 \times 10^{-6}/{}^\circ C$ --.

Signed and Sealed this

Eighteenth Day of June, 2002

*Attest:*

JAMES E. ROGAN
*Director of the United States Patent and Trademark Office*

*Attesting Officer*